(12) United States Patent
Lee et al.

(10) Patent No.: US 11,154,316 B2
(45) Date of Patent: Oct. 26, 2021

(54) SURGICAL INSTRUMENT

(71) Applicant: LIVSMED INC., Seongnam-si (KR)

(72) Inventors: Jung Joo Lee, Yongin-si (KR); Hee Jin Kim, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 16/973,351

(22) PCT Filed: Jun. 10, 2019

(86) PCT No.: PCT/KR2019/006957
§ 371 (c)(1),
(2) Date: Dec. 8, 2020

(87) PCT Pub. No.: WO2019/235905
PCT Pub. Date: Dec. 12, 2019

(65) Prior Publication Data
US 2021/0244429 A1     Aug. 12, 2021

Related U.S. Application Data

(60) Provisional application No. 62/682,577, filed on Jun. 8, 2018.

(51) Int. Cl.
*A61B 34/00* (2016.01)
*A61B 17/00* (2006.01)
*A61B 17/29* (2006.01)

(52) U.S. Cl.
CPC .......... *A61B 17/2909* (2013.01); *A61B 34/71* (2016.02); *A61B 2017/0042* (2013.01); *A61B 2017/2911* (2013.01); *A61B 2017/2912* (2013.01); *A61B 2017/2932* (2013.01)

(58) Field of Classification Search
CPC ................ A61B 17/2909; A61B 34/71; A61B 2017/2932; A61B 2017/2912; A61B 2017/2911; A61B 2017/0042; A61B 2017/2927; A61B 2017/00323
See application file for complete search history.

(56) References Cited

U.S. PATENT DOCUMENTS

| | | | |
|---|---|---|---|
| 6,394,998 | B1 | 5/2002 | Wallace et al. |
| 10,631,886 | B2 | 4/2020 | Lee et al. |
| 2007/0208375 | A1 | 9/2007 | Nishizawa et al. |
| 2008/0103492 | A1 | 5/2008 | Morley et al. |

(Continued)

FOREIGN PATENT DOCUMENTS

| | | |
|---|---|---|
| JP | 1984-102587 A | 6/1984 |
| JP | 2009-000179 A | 1/2009 |

(Continued)

*Primary Examiner* — Majid Jamialahmadi
(74) *Attorney, Agent, or Firm* — Novick, Kim & Lee, PLLC; Sang Ho Lee

(57) ABSTRACT

Provided is a surgical instrument including an end tool, a connection portion, a frame portion, a bridge portion, a manipulation portion, and a driving force transmission portion. The surgical instrument further includes a guide portion having one end portion provided on the bridge portion and the other end portion provided on the frame portion, surrounding a wire portion in a preset section, and guiding a movement path of the wire portion. The surgical instrument is manually operated for use in laparoscopic surgery or various surgical procedures.

16 Claims, 30 Drawing Sheets

(56) References Cited

U.S. PATENT DOCUMENTS

| | | |
|---|---|---|
| 2011/0106145 A1 | 5/2011 | Jeong et al. |
| 2015/0150635 A1 | 6/2015 | Kilroy et al. |
| 2017/0042560 A1* | 2/2017 | Lee .................. A61B 17/29 |
| 2020/0297445 A1 | 9/2020 | Lee et al. |

FOREIGN PATENT DOCUMENTS

| | | |
|---|---|---|
| JP | 2010-220786 A | 10/2010 |
| KR | 10-2009-0084110 A | 8/2009 |
| KR | 10-2011-0028613 A | 3/2011 |
| KR | 10-2015-0123056 A | 11/2015 |
| KR | 10-2016-0101538 A | 8/2016 |
| WO | 2009/096696 A2 | 8/2009 |

* cited by examiner

SURGICAL INSTRUMENT

TECHNICAL FIELD

The present disclosure relates to a surgical instrument, and more particularly, to a surgical instrument which may be manually operated for use in a laparoscopic surgery or other various surgeries.

BACKGROUND ART

Medically, surgery refers to a treatment of disease by using medical devices to cut, slit, or manipulate skin, mucous membrane, or other tissue. In particular, open surgery of cutting and opening the skin of a surgical site to treat, reshape, or remove organs therein causes bleeding, side effects, pain for the patient, and scars. Accordingly, recently, surgery using a robot or surgery which is performed by inserting only a medical device, for example, a laparoscope, a surgical instrument, a microsurgical microscope, or the like, by forming a predetermined hole in the skin, has been spotlighted as an alternative.

A surgical instrument is a tool for performing surgery at a surgical site by manipulating an end tool provided at one end of a shaft passing through a hole drilled in the skin by a doctor using a predetermined driving unit or by using a robot arm. The end tool provided at the surgical instrument performs rotating, gripping, cutting, or the like through a predetermined structure.

When an end tool is manipulated using a pulley or a wire in a surgical instrument according to the related art, the end tool is operated by using different axes as rotational center axes. However, as a movement path of a wire moving inside a surgical instrument is irregular, during the operation of any one end tool, another end tool's operation is affected such that accuracy may deteriorate.

The above-mentioned background technology is technical information acquired by the inventor for derivation of the present invention or acquired in the derivation process of the present invention, and is not necessarily a known technology disclosed to the general public before filing the present invention.

DESCRIPTION OF EMBODIMENTS

Technical Problem

Provided is a surgical instrument which may enable a motion of a manipulation portion and a motion of an end tool to be intuitively matched with each other by preventing influence between other different motions in the manipulation portion when a user manipulates the manipulation portion to perform an operation of the end tool.

In detail, provided is a guide portion which may guide a movement path of a pitch wire or a yaw wire for connecting a manipulation portion and an end tool and transmitting a driving force of the manipulation portion to the end tool, so that the length of the pitch wire or yaw wire in a section where the guide portion is provided may be maintained constant.

Solution to Problem

According to an embodiment of the present disclosure, a surgical instrument includes an end tool capable of rotating in at least two directions, a connection portion having a hollow inside and one end portion to which the end tool is connected, a frame portion having a hollow inside and coupled to another end portion of the connection portion opposite to the one end portion of the connection portion connected to the end tool, a bridge portion connected to the frame portion and capable of pitch motion with respect to the frame portion around a first axis as a pitch axis, a manipulation portion connected to the bridge portion and capable of yaw motion with respect to the bridge portion around a second axis as a yaw axis, the manipulation portion being capable of controlling a pitch motion, a yaw motion, and an actuation motion of the end tool, and a driving force transmission portion including at least one pulley portion provided on the bridge portion and the frame portion and at least one wire portion having one end portion connected to the end tool and capable of moving on the pulley portion, and transmitting a motion of the manipulation portion to the end tool, wherein a guide portion has one end portion provided on the bridge portion and another end portion provided on the frame portion, surrounds the wire portion in a preset section, and guides a movement path of the wire portion.

The manipulation portion, the frame portion, and the bridge portion may be rigid-linked with each other.

The guide portion may include a guide tube surrounding the wire portion in a preset section, and a pair of guide holders penetrated by the wire portion and disposed on the bridge portion and the frame portion to be coupled to each of both end portions of the guide tube.

The guide tube may include a flexible material.

The pulley portion may include a pitch pulley rotatable around the first axis as a rotation center axis and capable of rotating, and a yaw pulley rotatable around the second axis as a rotation center axis and capable of rotating.

The yaw pulley may be disposed closer to the end tool than the pitch pulley is.

The yaw pulley may be disposed spaced apart from the frame portion and provided on the manipulation portion to be rotated on the bridge portion, and the pitch pulley may be provided on the bridge portion to be rotated on the frame portion.

According to another embodiment of the present disclosure, a surgical instrument includes an end tool capable of rotating in at least two directions, a connection portion having a hollow inside and one end portion to which the end tool is connected, a frame portion having a hollow inside and coupled to another end portion of the connection portion opposite to the one end portion of the connection portion connected to the end tool, a bridge portion connected to the frame portion and capable of yaw motion with respect to the frame portion around a first axis as a yaw axis, a manipulation portion connected to the bridge portion and capable of pitch motion with respect to the bridge portion around a second axis as a pitch axis, the manipulation portion being capable of controlling a pitch motion, a yaw motion, and an actuation motion of the end tool, and a driving force transmission portion including at least one pulley portion provided on the bridge portion and the frame portion and at least one wire portion having one end portion connected to the end tool and capable of moving on the pulley portion, and transmitting a motion of the manipulation portion to the end tool, wherein a guide portion has one end portion provided on the bridge portion and another end portion provided on the frame portion, surrounds the wire portion in a preset section, and guides a movement path of the wire portion.

The pulley portion may include a yaw pulley rotatable around the first axis as a rotation center axis and capable of rotating, and a pitch pulley rotatably around the second axis as a rotation center axis and capable of rotating.

The pitch pulley may be disposed closer to the end tool than the yaw pulley is.

The pitch pulley may be disposed spaced apart from the frame portion and provided on the manipulation portion to be rotated on the bridge portion, and the yaw pulley may be provided on the bridge portion to be rotated on the frame portion.

Other aspects, features, and advantages than those described above will become apparent from the following drawings, claims, and detailed description of the disclosure.

Advantageous Effects of Disclosure

A surgical instrument according to the present disclosure may have an effect of intuitively transmitting a pitch motion, a yaw motion, and an actuation motion of a manipulation portion to an end tool.

Furthermore, the length of a wire portion may be maintained constant in a preset section by a guide portion.

Furthermore, as the length of the wire portion in the preset section is maintained constant, during any one of a pitch motion or a yaw motion, a change in the length or shape of the wire portion may be prevented from affecting another motion.

Furthermore, the guide portion may guide a path of the wire portion in the preset section.

Furthermore, as a frame portion, a bridge portion, and the manipulation portion are rigid-linked with one another, when a user moves the manipulation portion, the bridge portion and the frame portion connected to the manipulation portion may be moved together.

BEST MODE

Figure 1:
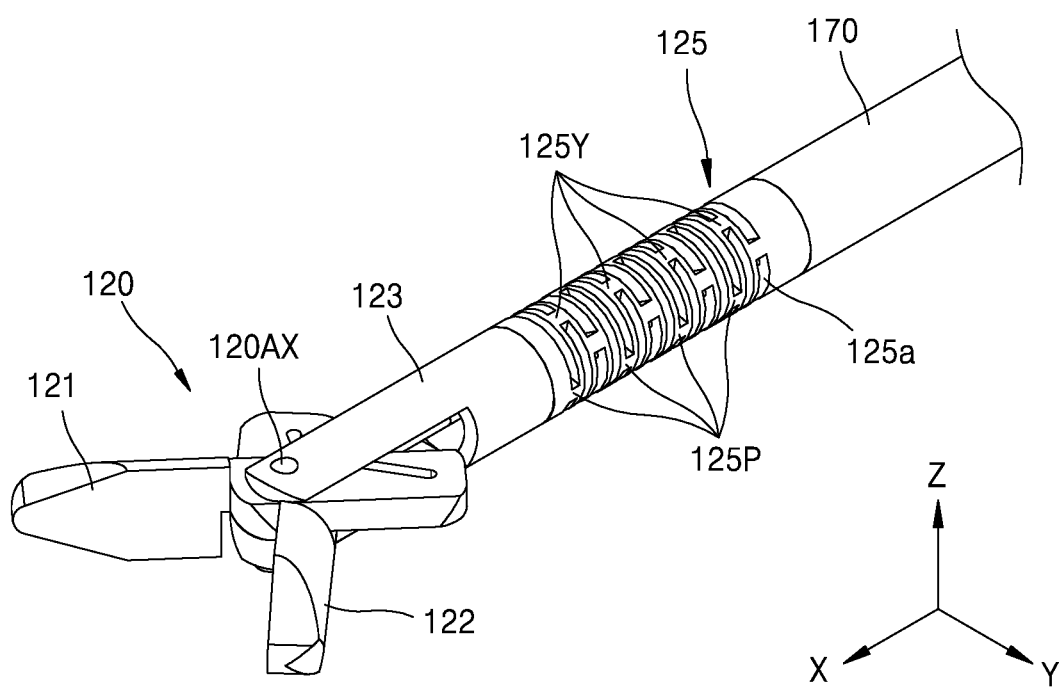
FIG. 1 is an assembled perspective view of an end tool according to an embodiment of the present disclosure.

As the disclosure allows for various changes and numerous embodiments, embodiments will be illustrated in the drawings and described in detail in the written description. However, this is not intended to limit the disclosure to particular modes of practice, and it is to be appreciated that all changes, equivalents, and substitutes that do not depart from the spirit and technical scope of the disclosure are encompassed in the disclosure. In the description of the disclosure, certain detailed explanations of the related art are omitted when it is deemed that they may unnecessarily obscure the essence of the disclosure.

While such terms as "first," "second," etc., may be used to describe various components, such components must not be limited to the above terms. The above terms are used only to distinguish one component from another.

The terms used in the specification are merely used to describe embodiments, and are not intended to limit the disclosure. An expression used in the singular encompasses the expression of the plural, unless it has a clearly different meaning in the context. In the specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, exemplary embodiments will be described in detail with reference to the accompanying drawings, and in the description with reference to the drawings, the same or corresponding constituents are indicated by the same reference numerals and redundant descriptions thereof are omitted.

Furthermore, in the description of various embodiments of the disclosure, it is not necessary to independently interpreted or worked each embodiment, and technical concepts described in the respective embodiments should be understood to be interpreted or worked by being combined to another embodiment that is individually described.

<Surgical Instrument According to an Embodiment>

Figure 2:
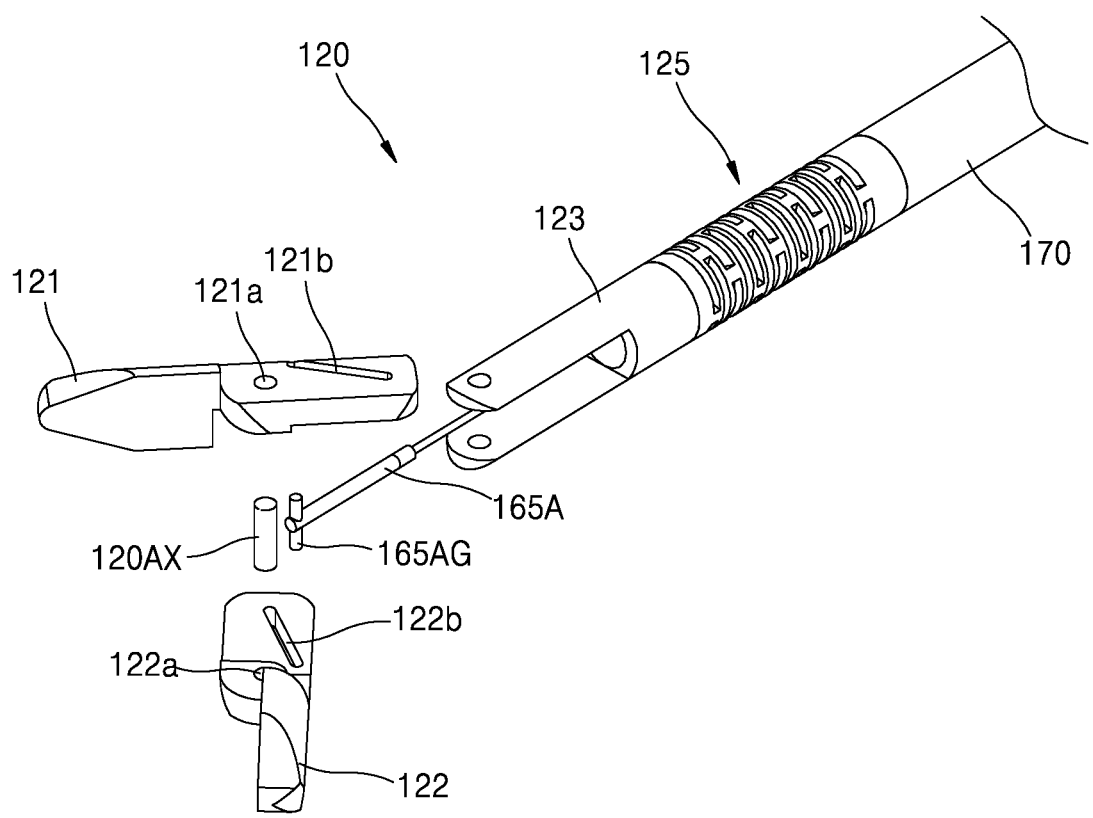
FIG. 2 is an exploded perspective view of the end tool of FIG. 1.
Figure 3A:
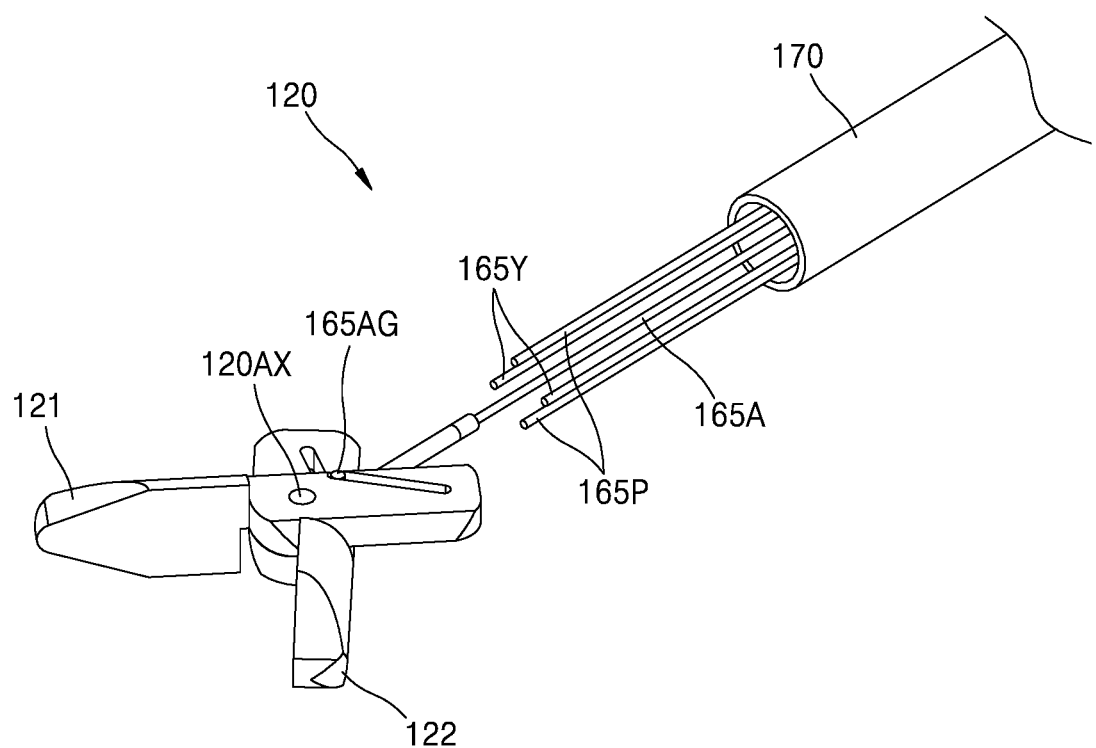
FIG. 3A is a perspective view of the end tool of FIG. 1 in which a jaw base and a joint member are omitted.
Figure 3B:
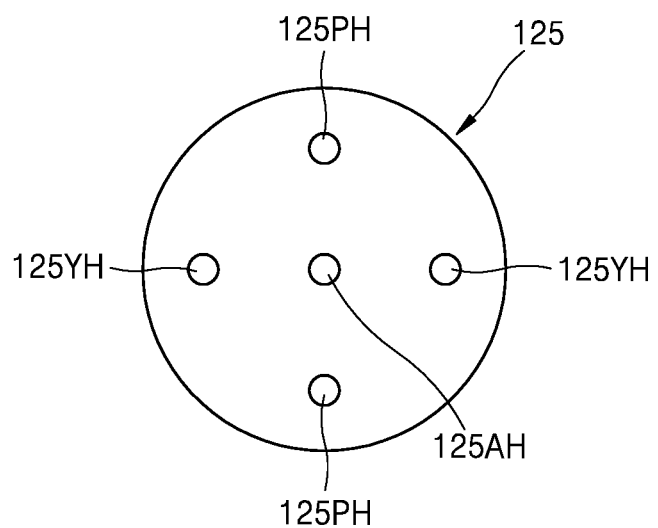
FIG. 3B is a front view of the joint member.
Figure 4:
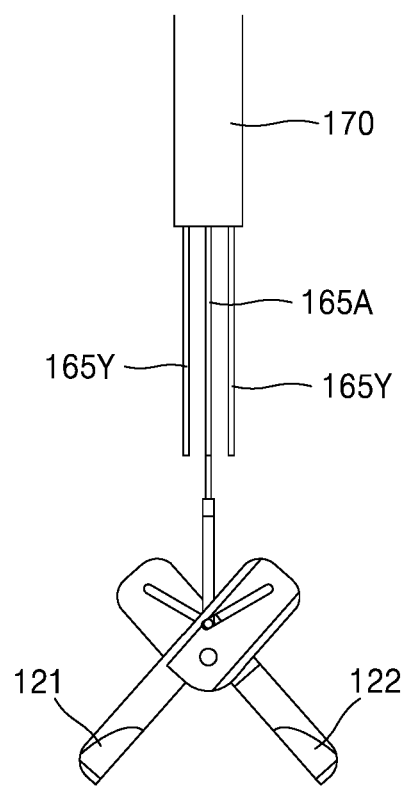
FIGS. 4 and 5 illustrate a yaw motion state of the end tool of FIG. 1.
Figure 5:
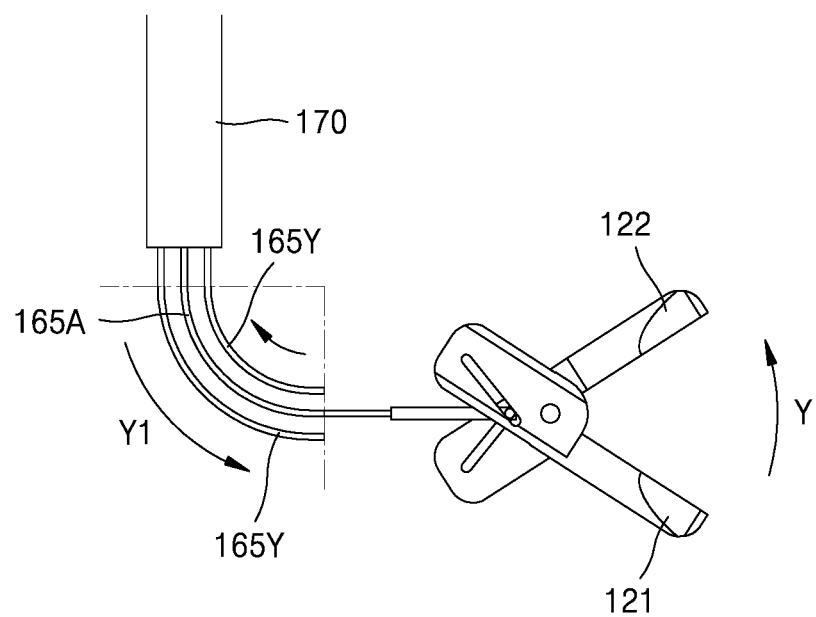
Figure 6:
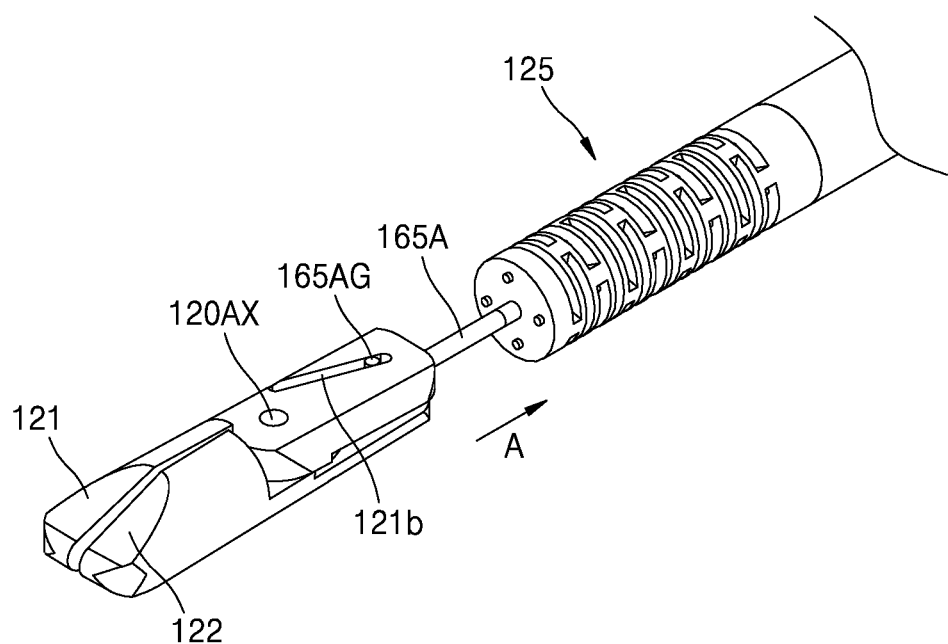
FIG. 6 illustrates a state in which the end tool of FIG. 1 is closed by an actuation motion.
Figure 7:
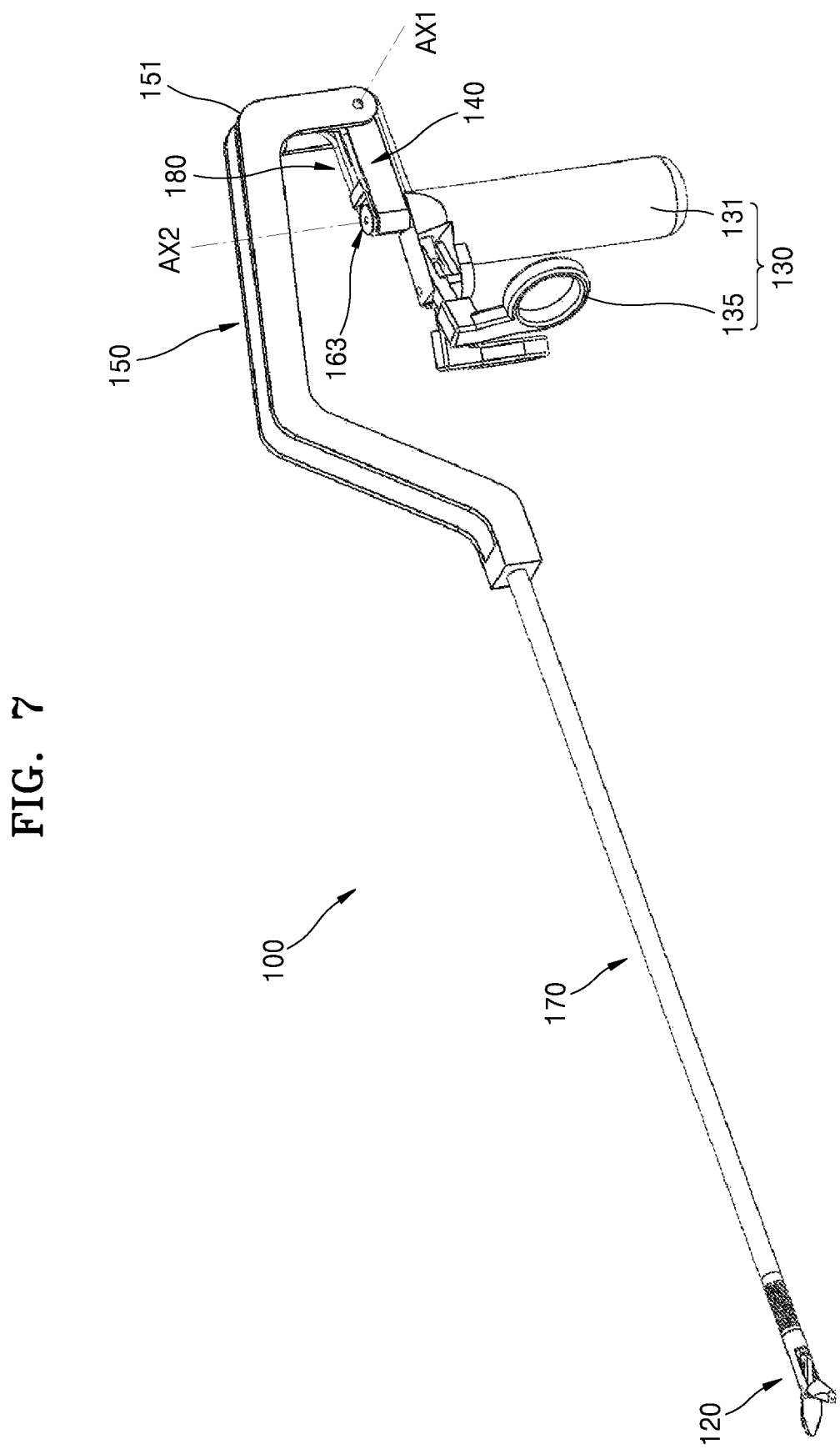
FIG. 7 is a perspective view of a surgical instrument according to an embodiment of the present disclosure.
Figure 8:
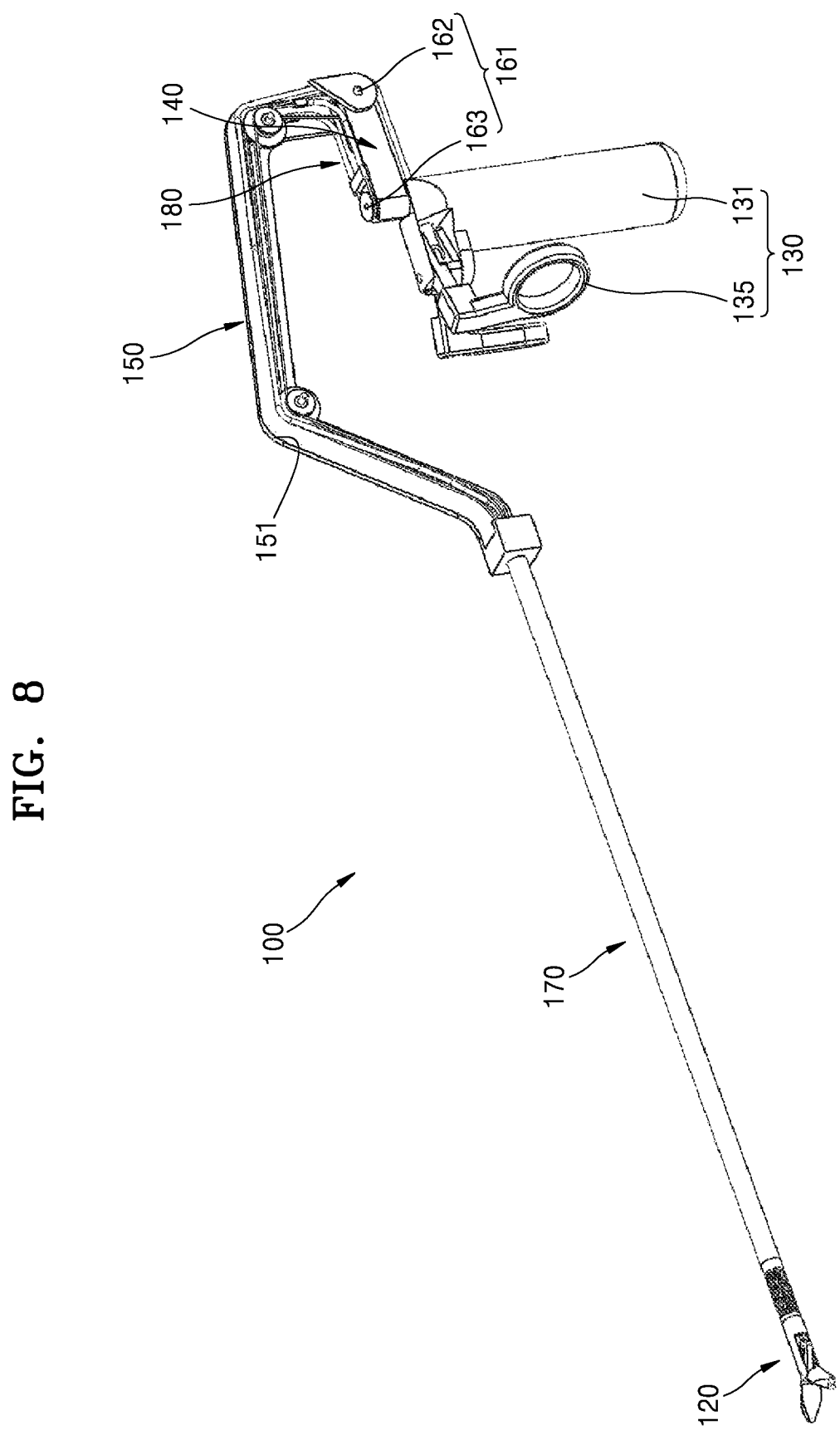
FIG. 8 is a partially cut-away view of a surgical instrument according to an embodiment of the present disclosure.
Figure 9:
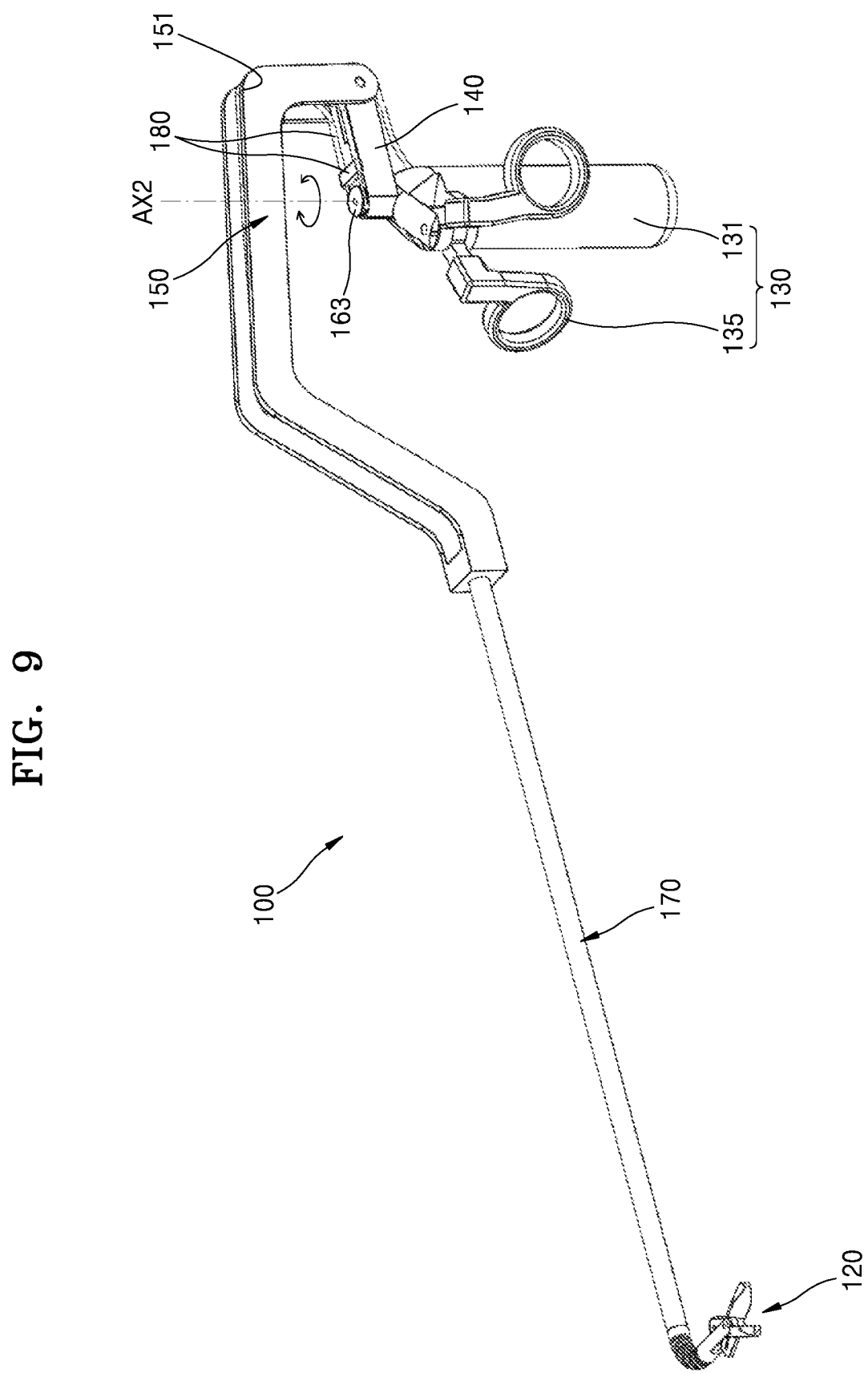
FIGS. 9 and 10 illustrate a motion state of an end tool according to an embodiment of the present disclosure.
Figure 10:
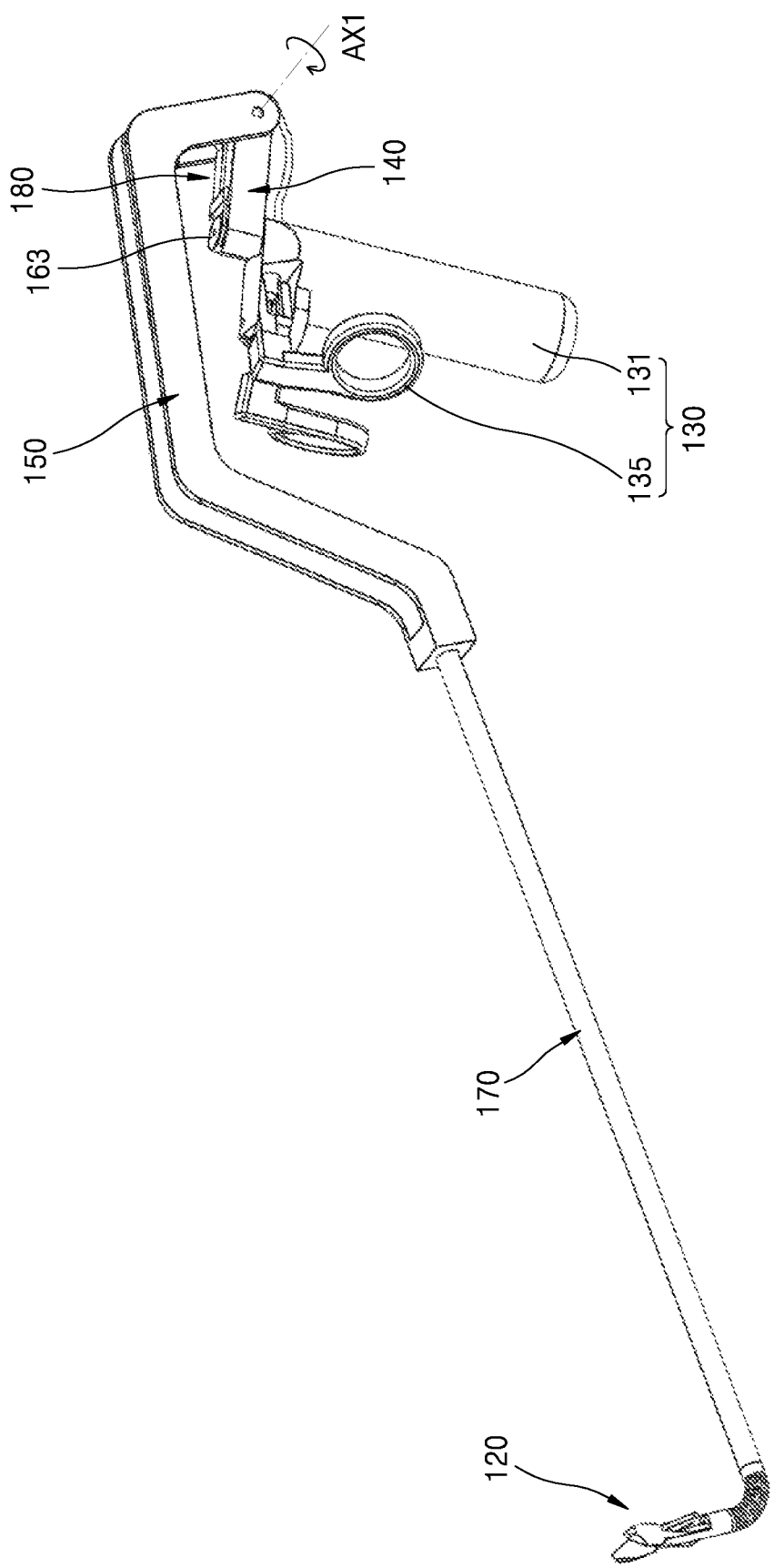
Figure 17:
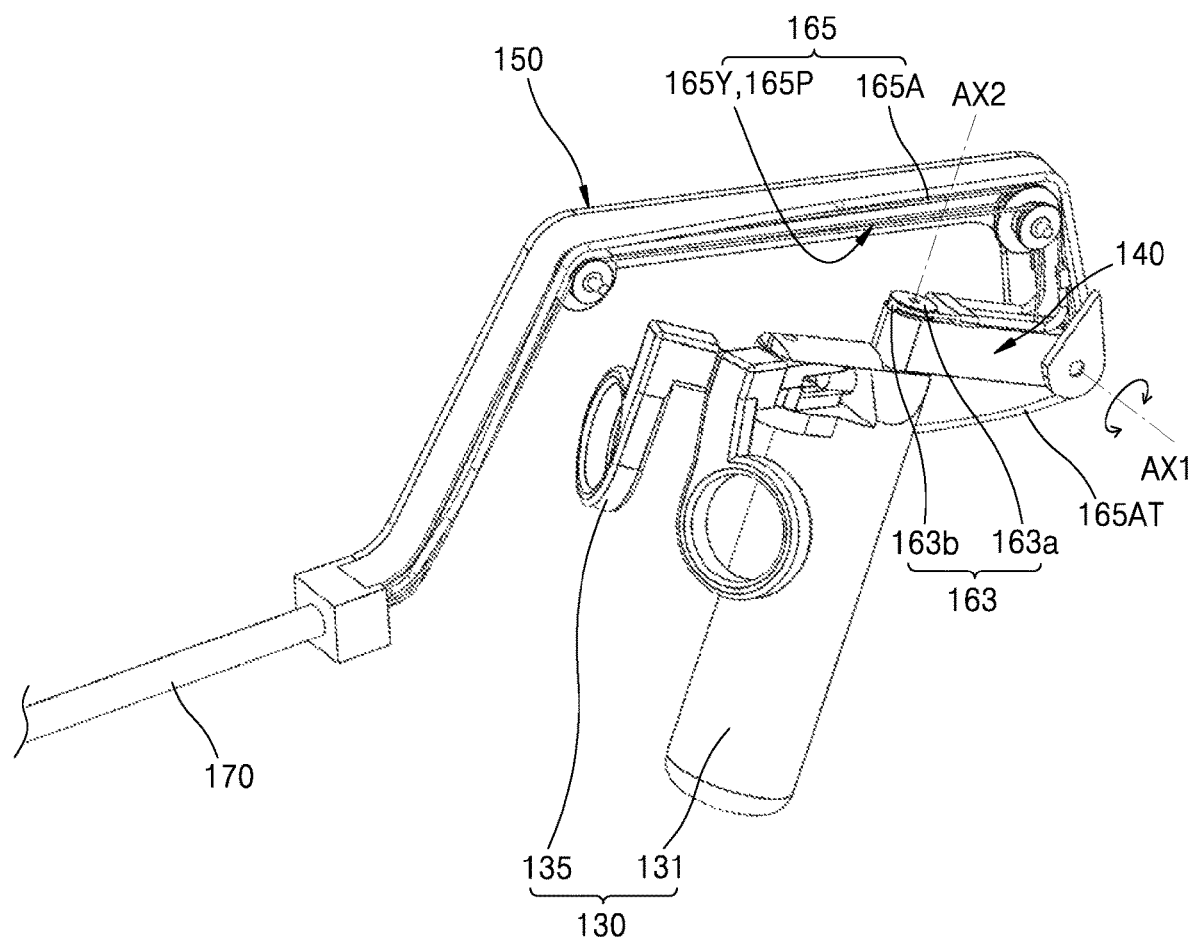
FIGS. 17 to 19 illustrate a pitch motion state of a surgical instrument according to an embodiment of the present disclosure.
Figure 18:
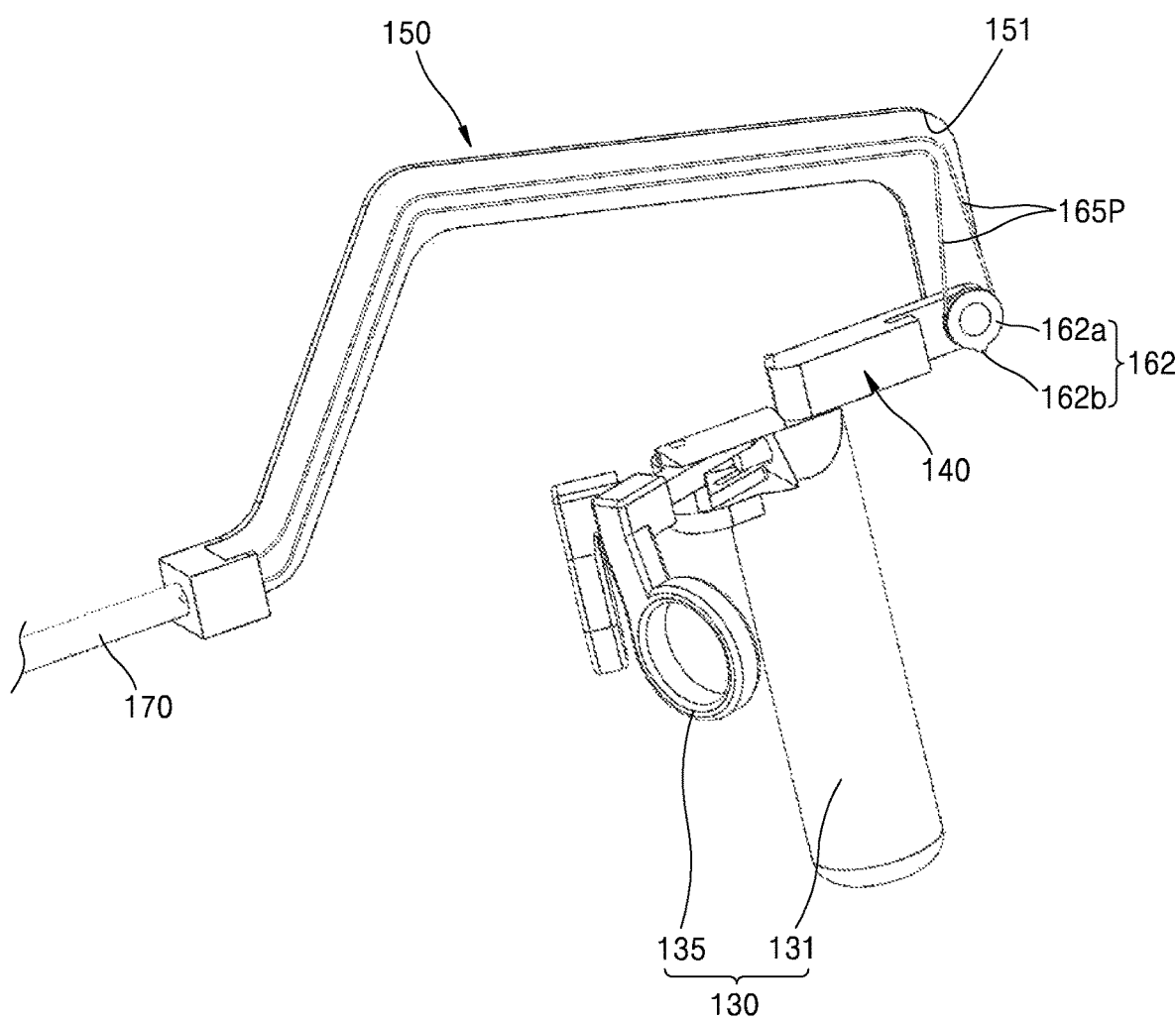
Figure 19:
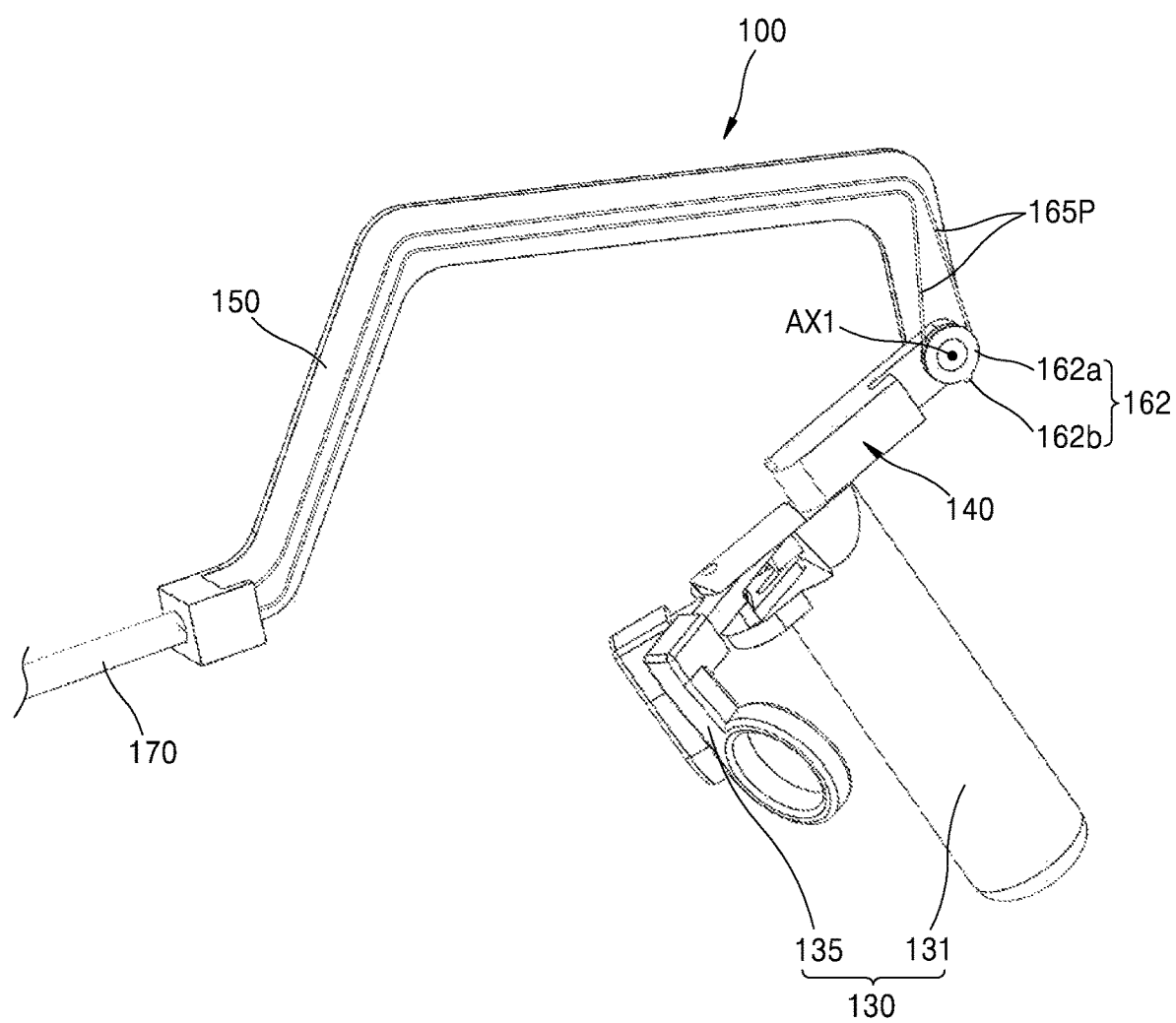

A surgical instrument according to an embodiment of the present disclosure is described with reference to the accompanying drawings. FIG. 1 is an assembled perspective view of an end tool according to an embodiment of the present disclosure. FIG. 2 is an exploded perspective view of the end tool of FIG. 1. FIG. 3A is a perspective view of the end tool of FIG. 1 in which a jaw base and a joint member are omitted. FIG. 3B is a front view of the joint member. FIGS. 4 and 5 illustrate a yaw motion state of the end tool of FIG. 1. FIG. 6 illustrates a state in which the end tool of FIG. 1 is closed by an actuation motion. FIG. 7 is a perspective view of a surgical instrument according to an embodiment of the present disclosure. FIG. 8 is a partially cut-away view of a surgical instrument according to an embodiment of the present disclosure. FIGS. 9 and 10 illustrate a motion state of an end tool according to an embodiment of the present disclosure. FIGS. 11 to 16 illustrate a yaw motion state of a surgical instrument according to an embodiment of the present disclosure. FIGS. 17 to 19 illustrate a pitch motion state of a surgical instrument according to an embodiment of the present disclosure.

Referring to FIGS. 1 to 19, a surgical instrument 100 according to an embodiment of the present disclosure may include an end tool 120, a manipulation portion 130, a bridge portion 140, a frame portion 150, a driving force transmission portion 160, a connection portion 170, and a guide portion 180.

In the specification about the surgical instrument 100 according to an embodiment of the present disclosure, a "first axis AX1" denotes a rotation center axis in performing a pitch motion, and a "second axis AX2" denotes a rotation center axis in performing a yaw motion.

Referring to FIGS. 1 to 7, the end tool 120 according to an embodiment of the present disclosure is rotatable in at least two directions and may be coupled to the connection portion 170 that is described later.

Referring to FIG. 1, the end tool 120 according to an embodiment of the present disclosure is connected to one end portion of the connection portion 170 that is described later (the left end portion in FIG. 7), and may be inserted in a surgical site to perform a motion necessary for surgery.

As an example of the end tool 120, a pair of jaws for performing a grip operation may be used. However, the concept of the present disclosure is not limited thereto, various devices for surgery may be used as the end tool 120.

For example, a configuration of a cantilever cautery may be used for the end tool 120. The end tool 120 configured as above is connected to the manipulation portion 130 by the driving force transmission portion 160, and receives a driving force of the manipulation portion 130 through the driving force transmission portion 160 to perform a motion necessary for surgery, such as gripping, cutting, suturing, or the like.

In other words, the end tool 120 is capable of performing a pitch motion, a yaw motion, and an actuation motion, which are described in detail later.

Referring to FIGS. 1 to 6, the end tool 120 applied to the surgical instrument 100 according to embodiments of the present disclosure is provided with a bendable joint member as a joint member 125.

In other words, the end tool 120 may include a first jaw 121, a second jaw 122, a jaw base 123, and the joint member 125. A wire portion 165 that is described later may include a pitch wire 165P, a yaw wire 165Y, and an actuation wire 165A.

A pitch motion may be performed by a movement of the pitch wire 165P connected to the joint member 125, and a yaw motion may be performed by a movement of the yaw wire 165Y connected to the joint member 125.

In this state, the actuation wire 165A may extend toward the end tool 120 between the pitch wire 165P and the yaw wire 165Y, and may be connected to axis through-holes 121a and 122a formed in each of the first jaw 121 and the second jaw 122.

As the actuation wire 165A advances and retreats, an actuation motion of opening and closing the two jaws 121 and 122 may be performed.

In this state, as the actuation wire 165A is provided at the center between two strands of the pitch wire 165P and two strands of the yaw wire 165Y, even when the pitch wire 165P and the yaw wire 165Y are moved by the pitch motion and the yaw motion, the actuation wire 165A is not affected.

When a pitch motion is performed as the lengths of the two strands of the pitch wire 165P vary, the yaw wire 165Y passing through the center between the two strands of the pitch wire 165P is not affected by the pitch motion. Likewise, when a yaw motion is performed as the lengths of the yaw wires 165Y at opposite sides vary, the pitch wire 165P passing through the center between the yaw wires 165Y at opposite sides is not affected by the yaw motion.

Referring to FIG. 1, the joint member 125 may be connected to one end portion of the connection portion 170 (the left end portion in FIG. 7). The joint member 125 according to an embodiment of the present disclosure may employ a bendable joint member.

The joint member 125 that is bendable has a hollow cylindrical shape, and a plurality of grooves 125a are formed in an outer circumferential surface of the joint member 125 in one direction (X-axis direction of FIG. 1) so as to be bendable.

In this state, ribs 125P and 125Y for guiding a bending direction of the joint member 125 may be formed in the middle of the grooves 125a.

In other words, while bending is not formed well at a location where the ribs 125P and 125Y are formed, bending is formed in a portion where the ribs 125P and 125Y are not formed.

In the joint member 125 according to an embodiment of the present disclosure, a first rib 125P for guiding bending of the joint member 125 in a first direction, that is, a pitch motion, and a second rib 125Y for guiding bending of the joint member 125 in a second direction, that is, a yaw motion, may be formed.

In this state, the second rib 125Y may be formed to be offset by a certain degree from the first rib 125P.

Furthermore, the first rib 125P is formed in the grooves 125a in an even number, and the second rib 125Y is formed in the grooves 125a in an odd number, so that the first rib 125P and the second rib 125Y may be alternately formed.

In other words, in FIG. 1, the first rib 125P is formed along both lateral surfaces of the joint member 125 so that the joint member 125 may be bent in a vertical direction.

Accordingly, although no actual rotation axis exists in the joint member 125, it may be assumed that rotation is performed around a Y-axis of FIG. 1. Accordingly, the joint member 125 may be a rotation center of a pitch motion.

Furthermore, the second rib 125Y is formed along upper and lower surfaces of the joint member 125, and the joint member 125 may be bent in a horizontal direction.

Accordingly, although no actual rotation axis exists in the joint member 125, it may be assumed that rotation is performed to the left and right around a Z-axis of FIG. 1.

Accordingly, the joint member 125 may be a rotation center of a yaw motion. The first rib 125P and the second rib 125Y are not necessarily formed on a vertical surface or a horizontal surface of the joint member 125, and may be formed to be offset by a certain degree from the vertical surface or horizontal surface of the joint member 125.

Both end portions of the pitch wire 165P and the yaw wire 165Y may be coupled to an end portion of the joint member 125 toward the first jaw 121 and the second jaw 122.

Accordingly, when any one end portion of the pitch wire 165P is pulled, one end portion of the joint member 125 connected thereto is pulled as well. Accordingly, the joint member 125 is rotated around the Y-axis of FIG. 1 so that a pitch motion is performed.

Likewise, when any one end portion of the yaw wire 165Y is pulled, one end portion of the joint member 125 connected thereto is pulled as well. Accordingly, the joint member 125 is rotated around the Z-axis of FIG. 1 so that a yaw motion is performed.

Referring to FIG. 3B, a pitch wire through-hole 125PH, a yaw wire through-hole 125YH, and an actuation wire through-hole 125AH are formed in one end portion of the joint member 125.

The pitch wire 165P extends from the connection portion 170 toward the end tool 120 by penetrating the pitch wire through-hole 125PH and is coupled to the other end portion of the joint member 125.

The yaw wire 165Y extends from the connection portion 170 toward the end tool 120 by penetrating the yaw wire through-hole 125YH and is coupled to the other end portion of the joint member 125.

The actuation wire 165A having penetrated the actuation wire through-hole 125AH is connected to an actuation guide pin 165AG.

In this state, the pitch wire through-hole 125PH, as illustrated in FIG. 3B, is formed in both end portions of the joint member 125 diametrically in the Z-axis direction.

The yaw wire through-hole 125YH, as illustrated in FIG. 3B, is formed in both end portions of the joint member 125 diametrically in the Y-axis direction. The actuation wire through-hole 125AH, as illustrated in FIG. 3B, is formed in the central portion of the joint member 125 to control an actuation motion.

As described above, the yaw wire 165Y performs a yaw motion as any one of both end portions thereof is pulled. In this state, as the actuation wire 165A and the pitch wire 165P passing through the center of both end portions of the yaw wire 165Y have no change in the length, the yaw motion may be performed independently of the actuation motion and the pitch motion.

Likewise, the pitch wire 165P performed a pitch motion as any one of both end portions thereof is pulled. In this state, as the actuation wire 165A and the yaw wire 165Y passing through the center of both end portions of the pitch wire 165P have no change in the length, the pitch motion may be performed independently of the actuation motion and the yaw motion.

The axis through-holes 121a and 122a are formed in the first jaw 121 and the second jaw 122, respectively, and an actuation axis 120AX may be inserted therein by penetrating the axis through-holes 121a and 122a of the first jaw 121 and the second jaw 122, respectively. As such, the first jaw 121 and the second jaw 122 are rotated around the actuation axis 120AX.

Guide holes 121b and 122b are respectively formed at one side of the axis through-holes 121a and 122a of the first jaw 121 and the second jaw 122, and the actuation guide pin 165AG is inserted into the axis through-holes 121a and 122a by passing through the guide holes 121b and 122b of the first jaw 121 and the second jaw 122.

As such, the actuation wire 165A is coupled to the actuation guide pin 165AG, and as the actuation wire 165A performs a linear reciprocating motion along the X-axis (based on FIG. 1), the actuation guide pin 165AG connected thereto performs a reciprocating motion along the guide holes 121b and 122b. Accordingly, the first jaw 121 and the second jaw 122 are rotated around the actuation axis 120AX so that an actuation motion is performed.

In other words, the actuation motion in which two jaws are simultaneously closed or opened may be performed through an advancing or retreating motion of the actuation wire 165A that is one.

As such, in the end tool 120 of the surgical instrument 100 according to embodiments of the present disclosure, as the pitch wire 165P of a pitch motion, the yaw wire 165Y for a yaw motion, and the actuation wire 165A for an actuation motion are separately formed, any one motion does not affect other motions.

Referring to FIGS. 4 and 5, the yaw wire 165Y for a yaw motion of the end tool 120 according to an embodiment of the present disclosure may connect the manipulation portion 130 to the joint member 125 of the end tool 120.

When a yaw pulley 163 that is described later is rotated counterclockwise around the second axis AX2 as a rotation center axis, the yaw wire 165Y at the end tool 120, when viewed in FIG. 5, the yaw wire 165Y at the left is pushed in a direction from the manipulation portion 130 toward the end tool 120 and the yaw wire 165Y at the right is pulled to be moved in a Y1 direction indicated by an arrow in FIG. 5.

Accordingly, the joint member 125 connected to the yaw wire 165Y, and the first jaw 121 and the second jaw 122 connected thereto, are rotated around the joint member 125 in the Y direction indicated by an arrow in FIG. 5, so that a yaw motion may be performed.

In other words, when the yaw pulley 163 rotates in one direction around the second axis AX2 as a rotation center axis through manipulation of the manipulation portion 130, the joint member 125 of the end tool 120, and the first jaw 121 and the second jaw 122 connected thereto, are rotated in the same direction, so that the manipulation direction of the manipulation portion 130 and the operating direction of the end tool 120 are intuitively matched with each other.

Next, the pitch motion of the present embodiment is described below.

Like the above-described yaw motion, the pitch wire 165P for a pitch motion of the end tool 120 connects the manipulation portion 130 to the joint member 125 of the end tool 120.

Figure 15:
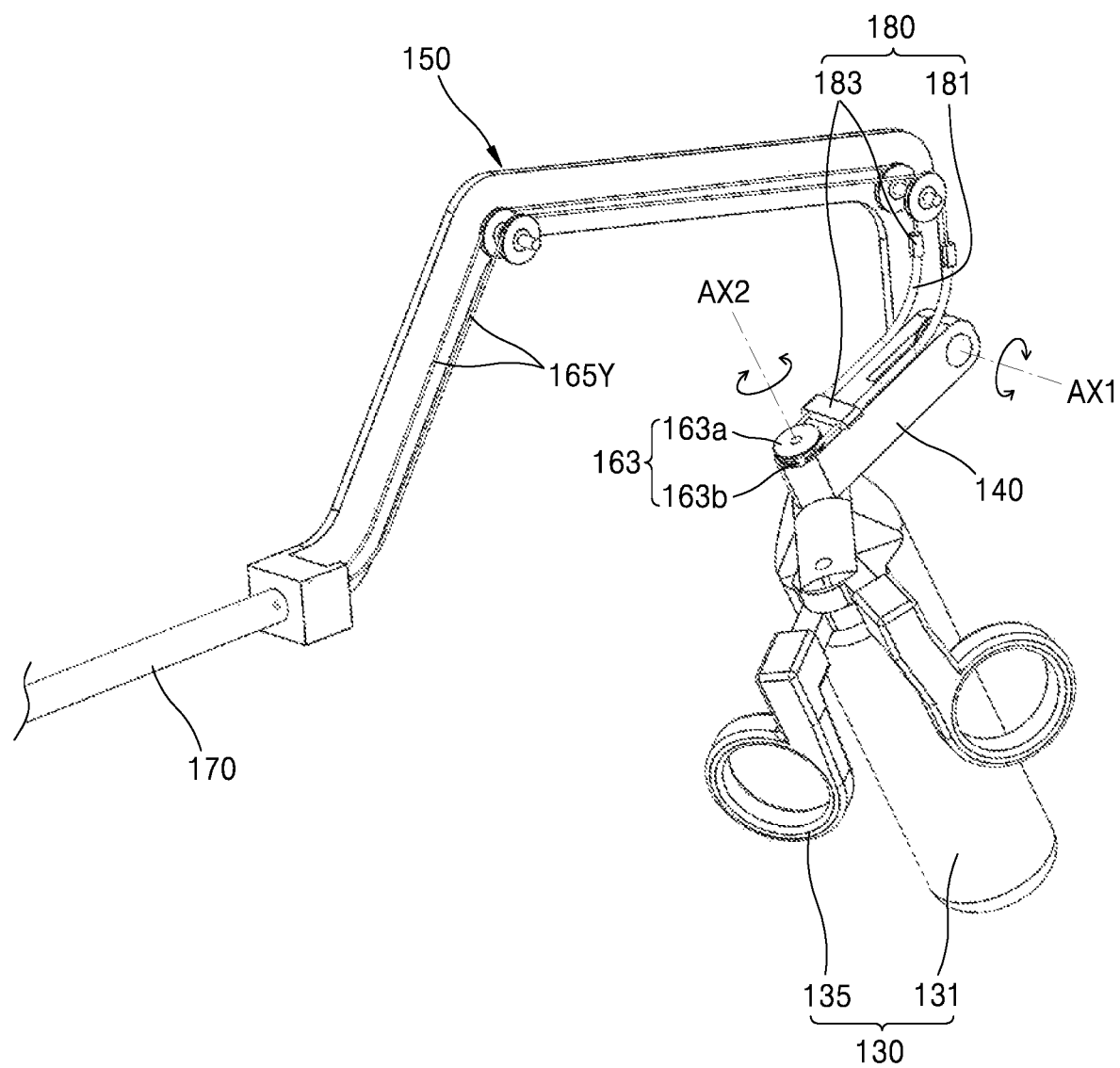

Referring to FIGS. 15, 17, and 18, as a pitch pulley 162 that is described later rotates around the first axis AX1 as a rotation center axis clockwise or counterclockwise, the pitch pulley 162, particularly, the pitch wire 165P coupled to a wire coupling portion 162b formed in a pulley main body 162a is moved. Accordingly, the joint member 125 connected to the pitch wire 165P, and the first jaw 121 and the second jaw 122 connected thereto, are rotated around the joint member 125, so that a pitch motion may be performed.

In other words, when the pitch pulley 162 rotates in one direction around the first axis AX1 as a rotation center, the joint member 125 of the end tool 120, and the first jaw 121 and the second jaw 122 connected thereto, are rotated in the same direction. Accordingly, the manipulation direction of the manipulation portion 130 and the operating direction of the end tool 120 are intuitively matched with each other.

Next, the actuation motion of the present embodiment is described below.

Figure 13:
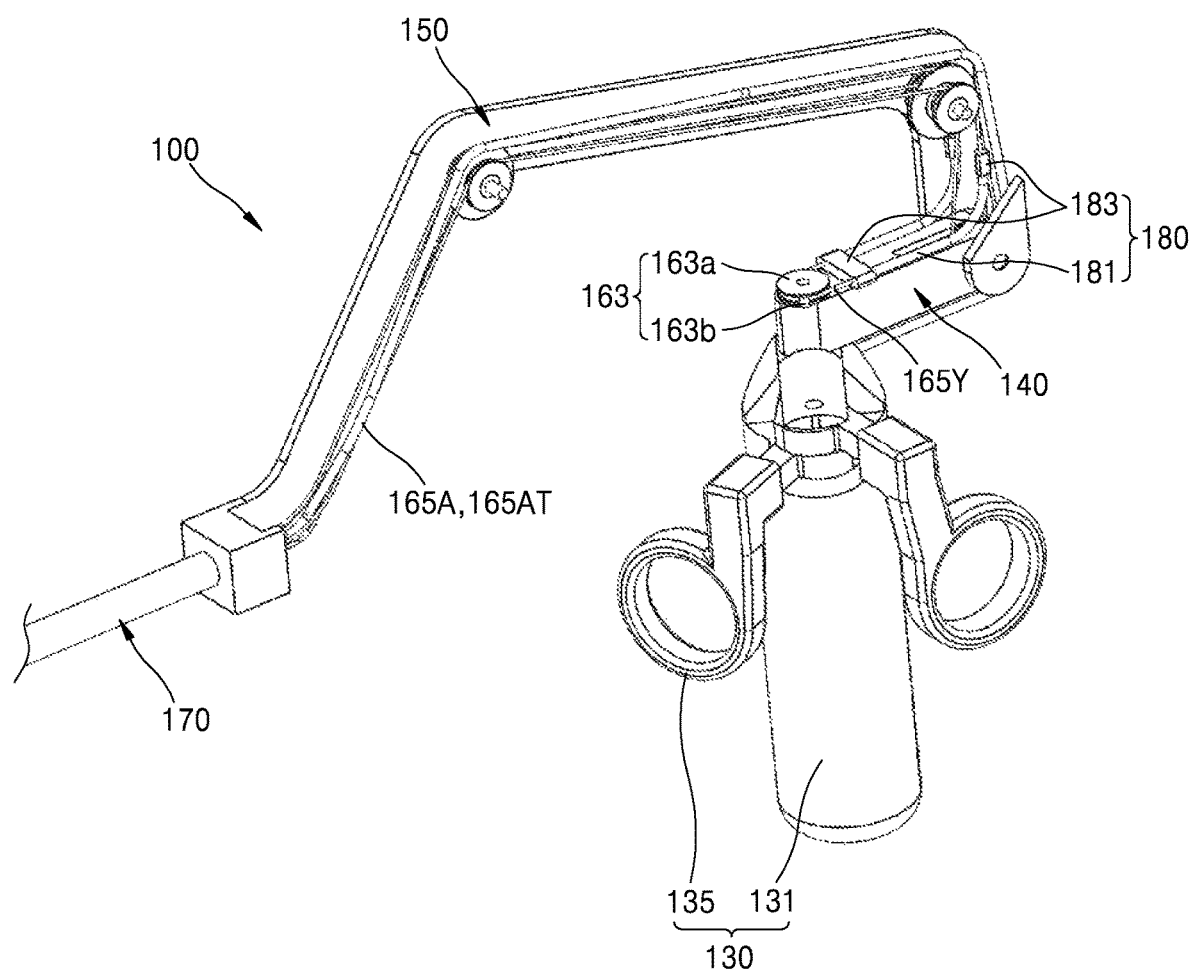

Referring to FIGS. 4, 6, and 13, the actuation wire 165A for an actuation motion of the end tool 120 may connect a finger ring portion 135 of the manipulation portion 130 to the actuation guide pin 165AG of the end tool 120.

Accordingly, when a user inserts fingers into the finger ring portion 135 and closes or opens the finger ring portion 135 by gripping the same, the actuation wire 165A connected to the finger ring portion 135 passes through the actuation wire through-hole 125AH formed in the joint member 125 and advances or retreats in the connection portion 170 in a direction toward the end tool 120.

The actuation wire 165A is inserted in an actuation tube 165AT and moves along a path of the actuation tube 165AT only so that a movement path of the actuation wire 165A is guided.

When the user inserts fingers into the manipulation portion 130, particularly, the finger ring portion 135, and opens the finger ring portion 135, the actuation wire 165A advances in a direction approaching the end tool 120 so that, as illustrated in FIG. 4, the first jaw 121 and the second jaw 122 are opened.

Furthermore, when the user inserts fingers into the manipulation portion 130, particularly, the finger ring portion 135, and closes the finger ring portion 135, the actuation wire 165A retreats in a direction away from the end tool 120 so that, as illustrated in FIG. 6, an actuation motion is performed in which the first jaw 121 and the second jaw 122 are closed.

Referring to FIGS. 7, 8, 11, 15, and 18, the manipulation portion 130 according to an embodiment of the present disclosure may include a manipulation main body 131 and the finger ring portion 135, which are capable of controlling a pitch motion, a yaw motion, and an actuation motion of the end tool 120.

The manipulation portion 130 according to an embodiment of the disclosure may be formed as a rigid-body. In the present disclosure, the "rigid-body" may denote an object having the shape and size that are not changed by an external force.

The manipulation main body 131 may have a cylindrical shape to be gripped by a user. However, the present disclosure is not limited thereto, and other various modifications such as a polygonal column may be possible.

Referring to FIG. 7, the manipulation main body 131 according to an embodiment of the present disclosure may be connected to the bridge portion 140 that is described later.

Figure 11:
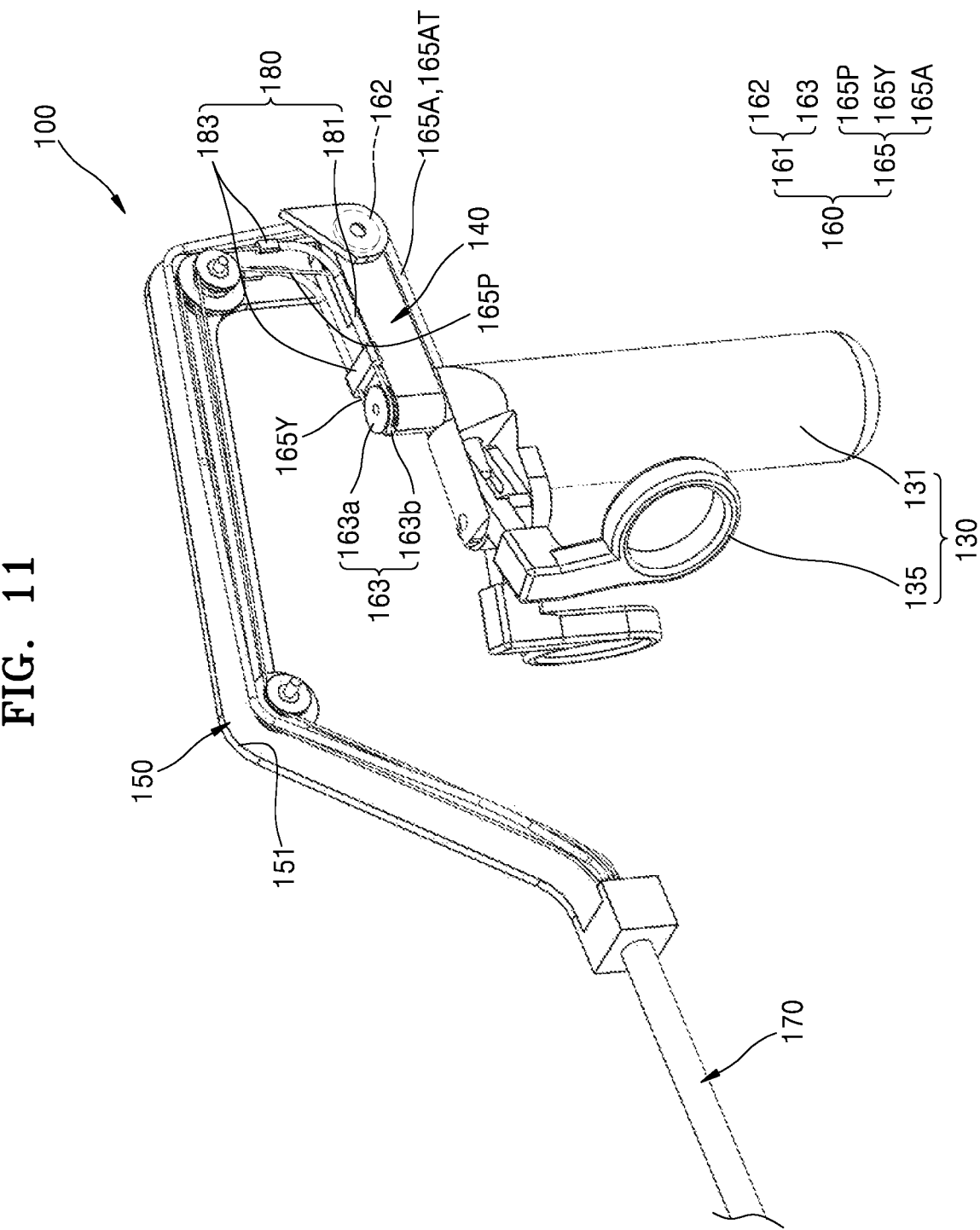
FIGS. 11 to 16 illustrate a yaw motion state of a surgical instrument according to an embodiment of the present disclosure.
Figure 12:
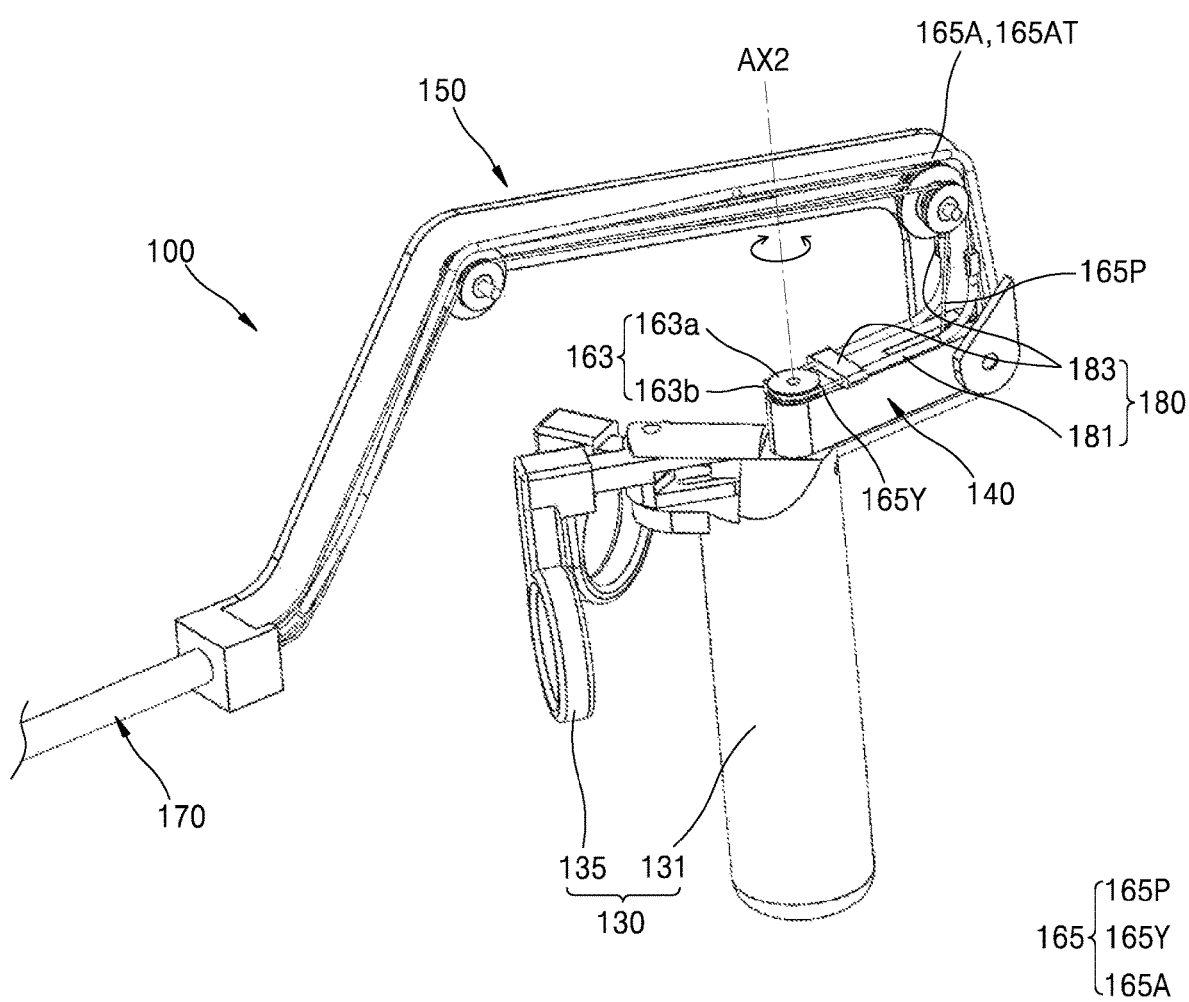

Referring to FIGS. 11 to 13, the finger ring portion 135 according to an embodiment of the present disclosure may have a hole portion (not referenced) to perform an actuation motion, that is, gripping, by inserting a user's finger.

As a user inserts fingers into the finger ring portion 135 and opens or closes the finger ring portion 135, the wire portion 165, particularly, the actuation wire 165A, which is described later, may be pushed or pulled.

In addition, the actuation motion of the manipulation portion 130 is transmitted to the end tool 120 by the driving force transmission portion 160, particularly, the actuation wire 165A, and thus the actuation motion of the end tool 120 is possible.

Referring to FIGS. 11 to 13, the manipulation portion 130, particularly, the manipulation main body 131 is rotatable around the second axis AX2 as a rotation center axis clockwise or counterclockwise, with respect to the bridge portion 140, and the rotation of the manipulation portion 130 may be associated with the rotation of the driving force transmission portion 160, particularly, the yaw pulley 163.

Accordingly, when the user rotates the manipulation portion 130 clockwise or counterclockwise, the yaw pulley 163 may be rotated around the second axis AX2 as a rotation center axis clockwise or counterclockwise.

The yaw pulley 163 according to an embodiment of the present disclosure may include a pulley main body 163a, and as the pulley main body 163a is rotated, a wire coupling portion 163b, which is fixedly located on the pulley main body 163a and to which the wire portion 165, particularly, the yaw wire 165Y, is coupled, is rotated clockwise or counterclockwise, and thus the yaw wire 165Y disposed on the yaw pulley 163 may be moved.

The yaw wire 165Y disposed at each of both sides with respect to the wire coupling portion 163b formed on the pulley main body 163a is moved in a different direction in the frame portion 150, that is, the connection portion 170 that is described later, and the driving force of the yaw wire 165Y s transmitted to the end tool 120 so that the yaw motion of the end tool 120 is possible.

Referring to FIGS. 7, 8, 11, 15, and 18, the bridge portion 140 according to an embodiment of the present disclosure has one end portion connected to the frame portion 150, and is capable of pitch motion relative to the frame portion 150 with respect to the first axis AX1 as a pitch axis.

The other end portion of the bridge portion 140, which corresponds to the one end portion connected to the frame portion 150, is connected to the manipulation portion 130, and the bridge portion 140 may be formed to be capable of yaw motion with the manipulation portion 130, with respect to the second axis AX2 as a yaw axis.

In other words, the manipulation portion 130 may be formed to be capable of yaw motion with respect to the bridge portion 140.

The bridge portion 140, like the manipulation portion 130, may be formed as a rigid-body, and the manipulation portion 130 and the frame portion 150 may be rigid-linked with each other.

In the present specification, the "rigid-link" means that independent elements are respectively formed as rigid-bodies and the elements are connected to each other.

Figure 16:
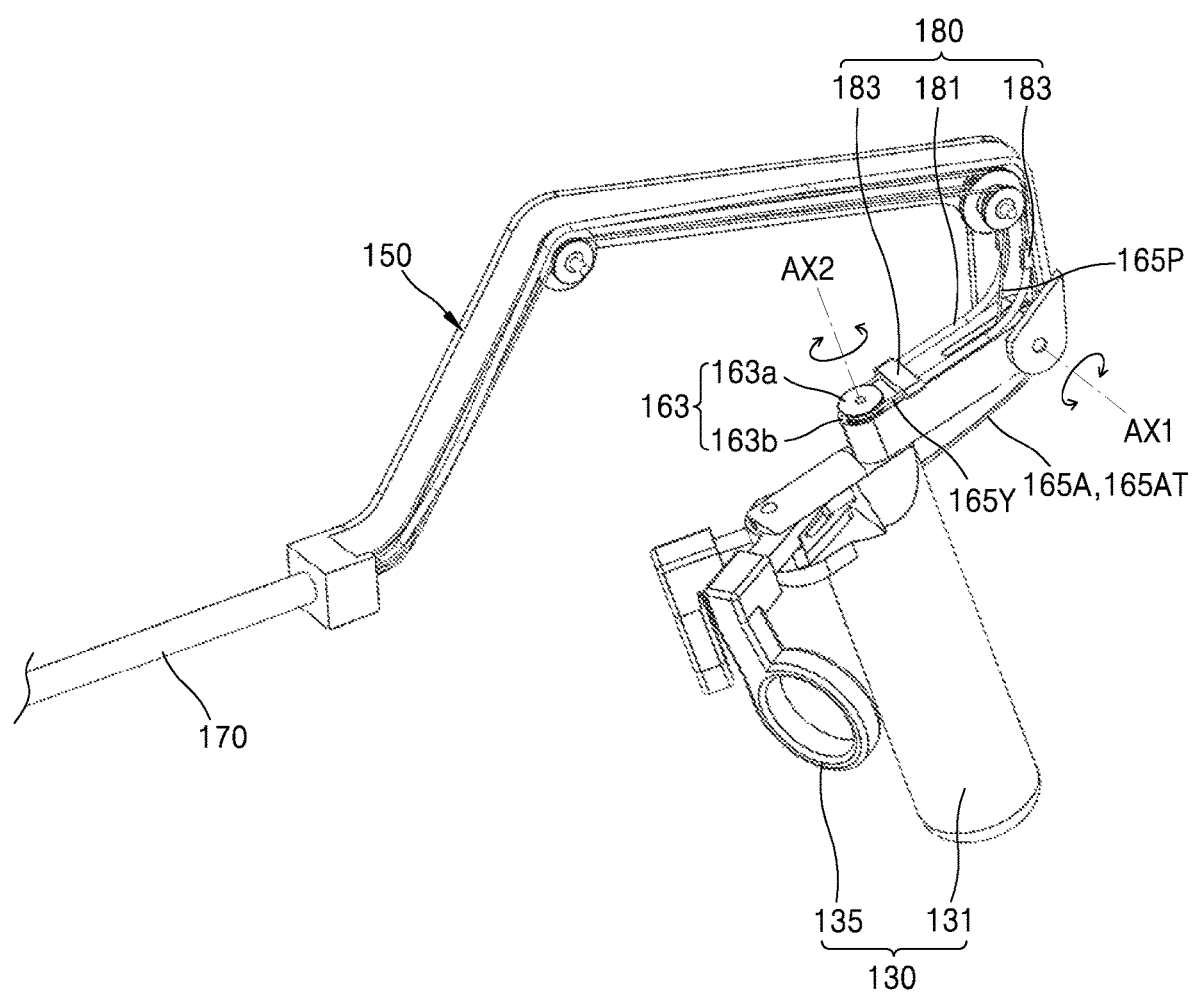

Referring to FIGS. 7, 16, and 18, the bridge portion 140 according to an embodiment of the present disclosure may be connected to the frame portion 150 that is described later, and is capable of pitch motion relative to the frame portion 150 with respect to the first axis AX1 as a pitch axis.

In other words, assuming that the location of the frame portion 150 is fixed, the user may rotate the manipulation portion 130 and the bridge portion 140 around the first axis AX1 as a rotation center axis clockwise or counterclockwise with respect to the frame portion 150.

The pitch pulley 162 is connected to the bridge portion 140, and particularly, the pulley main body 162a may be fixedly located at and coupled to the bridge portion 140.

Accordingly, when the bridge portion 140 rotates around the first axis AX1 as a rotation center axis clockwise or counterclockwise, with respect to the frame portion 150, the pulley main body 162a coupled to the bridge portion 140 is also capable of rotating around the first axis AX1 as a rotation center axis, with respect to the frame portion 150.

In the pulley main body 162a according to an embodiment of the present disclosure, the wire coupling portion 162b formed at a preset position and to which the pitch wire 165P is coupled may also rotate around the first axis AX1 as a rotation center axis clockwise or counterclockwise.

Accordingly, the pitch wire 165P disposed at each of both sides with respect to the wire coupling portion 162b formed in the pulley main body 162a may move in the frame portion 150 and the connection portion 170 in a different movement direction.

The movement of the pitch wire 165P is transmitted to the end tool 120 so that the pitch motion of the end tool 120 is possible.

Referring to FIGS. 7, 8, 11, 15, and 18, the frame portion 150 according to an embodiment of the present disclosure is coupled to the other end portion facing the one end portion of the connection portion 170 connected to the end tool 120, and the inside of the frame portion 150 is empty.

The frame portion 150 according to an embodiment of the present disclosure is connected to the bridge portion 140, and is capable of pitch motion with the bridge portion 140 with respect to the first axis AX1 as a pitch axis. In other words, the bridge portion 140 is capable of pitch motion with respect to the frame portion 150.

On end portion of the frame portion 150 is connected to the bridge portion 140 to be capable of rotating relative thereto, and the other end portion thereof may be connected to the connection portion 170.

The frame portion 150 according to an embodiment of the present disclosure may be formed as a rigid-body, like the manipulation portion 130 and the bridge portion 140.

As the manipulation portion 130, the bridge portion 140, and the frame portion 150 are formed as rigid-bodies, the manipulation portion 130, the bridge portion 140, and the frame portion 150 may be rigid-linked.

Accordingly, the positions of the bridge portion 140 and the frame portion 150 which are rigid-linked with the manipulation portion 130 are determined only when the user grips the manipulation portion 130, the bridge portion 140 and the frame portion 150 may be moved together when the manipulation portion 130 is moved.

The inside of the frame portion 150 is empty, and the wire portion 165, particularly, the pitch wire 165P, the yaw wire 165Y, and the actuation wire 165A, may be provided in the frame portion 150.

The pitch wire 165P, the yaw wire 165Y, and the actuation wire 165A may move inside the frame portion 150, and at least one pulley (not referenced) for guiding the movement path of the wire portion 165 may be provided on the frame portion 150.

The wire portion 165, the pitch wire 165P, the yaw wire 165Y, and the actuation wire 165A according to an embodiment of the present disclosure may be connected to the end tool 120 by extending from the manipulation portion 130 and the bridge portion 140 and passing through the frame portion 150 and the connection portion 170 connected to the frame portion 150.

Accordingly, the motions, particularly, the pitch motion, the yaw motion, and the actuation motion, which are performed while the user gripping the manipulation portion 130, may be intuitively transmitted to the end tool 120.

Referring to FIG. 7, in the frame portion 150 according to an embodiment of the present disclosure, at least one bending portion 151 may be formed in the lengthwise direction that is formed by extending.

Referring to FIGS. 7, 8, 11, 15, and 18, the driving force transmission portion 160 according to an embodiment of the present disclosure transmits a motion of the manipulation portion 130 to the end tool 120 and may include a pulley portion 161 and the wire portion 165.

The pulley portion 161 according to an embodiment of the present disclosure is provided on the bridge portion 140 and the frame portion 150 and may include at least one pulley portion. The pulley portion 161 may include the pitch pulley 162 and the yaw pulley 163.

Referring to FIGS. 11 and 18, the pitch pulley 162 according to an embodiment of the present disclosure is rotatable around the first axis AX1 as a rotation center axis, and may include the pulley main body 162a and the wire coupling portion 162b.

The pulley main body 162a is connected to the bridge portion 140, and when the user grips the manipulation portion 130 and rotates the manipulation portion 130 around the first axis AX1 as a rotation center axis clockwise or counterclockwise, the pulley main body 162a may be rotated clockwise or counterclockwise in association therewith.

Accordingly, the pulley main body 162a rotates clockwise or counterclockwise on the frame portion 150.

Referring to FIG. 18, the wire coupling portion 162b may be formed in the pulley main body 162a at a preset position so that the wire portion 165, particularly, the pitch wire 165P, may be coupled thereto.

In the present disclosure, although the wire coupling portion 162b protrudes along an outer circumferential surface of the pulley main body 162a, the present disclosure is not limited thereto, and various modifications are possible within a technical concept that the pitch wire 165P is coupled to the pulley main body 162a so that the position of one end portion of the pitch wire 165P is fixed.

Accordingly, when the user grips the manipulation portion 130, particularly, the manipulation main body 131, and rotates the manipulation portion 130 and the bridge portion 140 connected to the manipulation portion 130 around the first axis AX1 as a rotation center axis with respect to the frame portion 150, the pitch pulley 162 in association with the manipulation portion 130 and the bridge portion 140 may be rotated around the first axis AX1 as a rotation center clockwise or counterclockwise.

In other words, the wire coupling portion 162b formed in the pulley main body 162a is rotated around the first axis AX1 as a rotation center axis clockwise or counterclockwise, the wire portion 165, particularly, the pitch wire 165P, disposed on the pulley main body 162a at both sides with respect to the wire coupling portion 162b is wound or released so as to be moved inside the frame portion 150 and the connection portion 170, and thus the motion of the manipulation portion 130 may be transmitted as the pitch motion of the end tool 120.

Referring to FIGS. 11 and 18, the yaw pulley 163 according to an embodiment of the present disclosure is rotatable around the second axis AX2 as the rotation center axis, and may include the pulley main body 163a and the wire coupling portion 163b. The yaw pulley 163 may be disposed closer to the end tool 120 than the pitch pulley 162 is.

The pulley main body 163a is connected to the manipulation portion 130, and when the user rotates the manipulation portion 130, particularly, the manipulation main body 131, around the second axis AX2 as a rotation center axis clockwise or counterclockwise, the pulley main body 163a may be rotated clockwise or counterclockwise in association therewith.

Accordingly, the pulley main body 163a is rotated clockwise or counterclockwise on the bridge portion 140.

Referring to FIG. 12, the wire coupling portion 163b may be formed in the pulley main body 163a at a preset position so that the wire portion 165, particularly, the yaw wire 165Y, is coupled thereto.

In the present disclosure, although the wire coupling portion 163b protrudes along an outer circumferential surface of the pulley main body 163a, the present disclosure is not limited thereto, and various modifications are possible within a technical concept that the yaw wire 165Y is coupled to the pulley main body 163a so that the position of one end portion of the yaw wire 165Y is fixed.

Accordingly, when the user grips the manipulation portion 130 and rotates the manipulation portion 130 around the second axis AX2 as a rotation center axis clockwise or counterclockwise, the yaw pulley 163 in association with the manipulation portion 130 may be rotated around the second axis AX2 as a rotation center axis clockwise or counterclockwise.

In other words, the wire coupling portion 163b formed on the pulley main body 163a is rotated around the second axis AX2 as a rotation center axis clockwise or counterclockwise, the wire portion 165, particularly, the yaw wire 165Y, disposed on the pulley main body 163a at both sides with respect to the wire coupling portion 163b is wound or released so as to be moved inside the frame portion 150 and the connection portion 170, and thus the yaw motion of the manipulation portion 130 may be transmitted as the yaw motion of the end tool 120.

Referring to FIGS. 11 and 18, the wire portion 165, particularly, the pitch wire 165P and the yaw wire 165Y, according to an embodiment of the present disclosure are moved inside the frame portion 150 and the connection portion 170, and a user's motion in the manipulation portion 130 may be transmitted to the end tool 120.

At least one pulley is provided inside the frame portion 150 according to an embodiment of the present disclosure, and as the pitch wire 165P and the yaw wire 165Y are moved on the pulley, a movement path may be guided.

Referring to FIGS. 3 and 17, the actuation wire 165A according to an embodiment of the disclosure is connected to the manipulation portion 130, particularly, the finger ring portion 135, and when the user inserts fingers into the finger ring portion 135 and grips the finger ring portion 135, the actuation wire 165A may be pushed or pulled.

As the user inserts fingers into the finger ring portion 135 and grips the finger ring portion 135, the actuation wire 165A connected to the finger ring portion 135 is moved inside the frame portion 150 and the connection portion 170 so that the gripping of the finger ring portion 135 may be transmitted as the gripping of the end tool 120.

The actuation wire 165A may be inserted into the inside of the actuation tube 165AT that includes a flexible material, and the actuation tube 165AT guides the movement path of the actuation wire 165A, thereby preventing interference between the pitch wire 165P and the yaw wire 165Y.

Referring to FIGS. 7, 8, 11, 15, and 18, the connection portion 170 according to an embodiment of the present disclosure has a hollow tube-like shape, and the end tool 120 is coupled to one end portion thereof and the frame portion 150 is coupled to the other end portion thereof so that the end tool 120 and the frame portion 150 may be connected to each other.

The wire portion 165, particularly, the pitch wire 165P, the yaw wire 165Y, and the actuation wire 165A, passes through the connection portion 170 from the frame portion 150 and may be connected to the end tool 120.

As the wire portion 165 is moved inside the frame portion 150 and the connection portion 170 according to the user's motion in the manipulation portion 130, the pitch motion, the yaw motion, and the actuation motion in the manipulation portion 130 or the bridge portion 140 may be transmitted to the end tool 120.

Referring to FIGS. 7, 11, and 17, the guide portion 180 according to an embodiment of the present disclosure may have one end portion provided in the bridge portion 140 and the other end portion provided in the frame portion 150, surround the wire portion 165 in a preset section, and guide the movement path of the wire portion 165.

Figure 14:
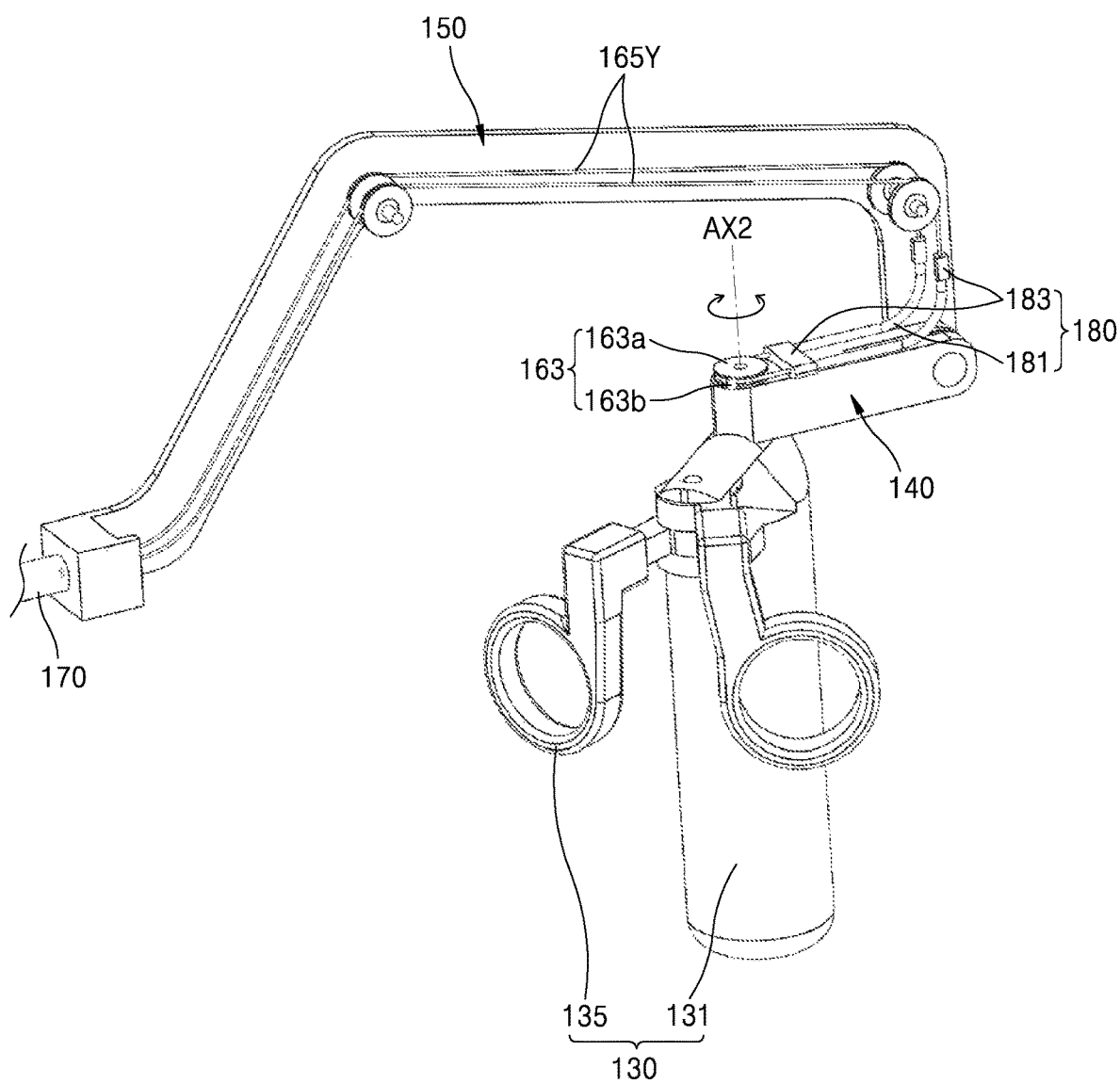

Referring to FIGS. 14 and 15, the guide portion 180 according to an embodiment of the present disclosure may include a guide tube 181 and a pair of guide holders 183.

The guide tube 181 according to an embodiment of the present disclosure surrounds the wire portion 165, particularly, the yaw wire 165Y, in a preset section, and the yaw wire 165Y may be moved inside the guide tube 181.

The yaw wire 165Y is inserted into the guide tube 181, and thus the yaw wire 165Y may be prevented from deviating from a preset path inside the guide tube 181.

In addition, as the length of the guide portion 180, particularly, the guide tube 181, is constant, the length of a portion of the yaw wire 165Y inserted into the guide tube 181 is constant as long as the length of the guide tube 181.

Both end portions of the guide tube 181 according to an embodiment of the present disclosure may be coupled to the pair of guide holders 183 that are described later.

Accordingly, the length of the guide tube 181 connecting between the pair of guide holders 183, which are respectively fixedly coupled to the bridge portion 140 and the frame portion 150, may be fixed, and thus a portion of the yaw wire 165Y corresponding to the length of the guide tube 181 may be disposed in the guide tube 181.

The guide tube 181 according to an embodiment of the present disclosure may be formed of a flexible material. Accordingly, when the bridge portion 140 and the frame portion 150 perform a pitch motion by rotating relative to each other around the first axis AX1 as a rotation center axis, the shape of the guide tube 181 may be deformed according thereto.

Referring to FIGS. 14 and 15, the pair of guide holders 183 according to an embodiment of the present disclosure are where the wire portion 165, particularly, the yaw wire 165Y, penetrates, and may be disposed in the bridge portion 140 and the frame portion 150 and coupled to both end portions of the guide tube 181.

The pair of guide holders 183 are respectively fixed to of the bridge portion 140 and the frame portion 150, and the guide tube 181, which is formed as long as a preset length, may be connected between the pair of guide holders 183 respectively disposed in the bridge portion 140 and the frame portion 150.

Due to the guide tube 181 having a preset length and the pair of guide holders 183 respectively fixed to the bridge portion 140 and the frame portion 150 and coupled to both end portions of the guide tube 181, when the bridge portion 140 and the frame portion 150 perform a pitch motion around the first axis AX1 as a rotation center axis so that the positions of the pair of guide holders 183 are changed according to the rotation of the frame portion 150, a distance between the pair of guide holders 183, that is, the length of the guide tube 181, may be maintained constant.

In addition, as the length of the guide tube 181 is maintained constant, even when relative positions of the bridge portion 140 and the frame portion 150 are changed, the length of the wire portion 165, particularly, the yaw wire 165Y, located inside the guide tube 181 may be maintained constant.

In other words, during the pitch motion of the bridge portion 140 connected to the manipulation portion 130 and the frame portion 150 rotating relative to each other around the first axis AX1 as a rotation center axis, the length of the yaw wire 165Y may be maintained constant in a preset section, particularly, the length of the guide portion 180. During the pitch motion, the yaw motion is not affected, and thus the pitch motion and the yaw motion may be performed independently of each other.

<Surgical Instrument According to Another Embodiment>

Figure 20:
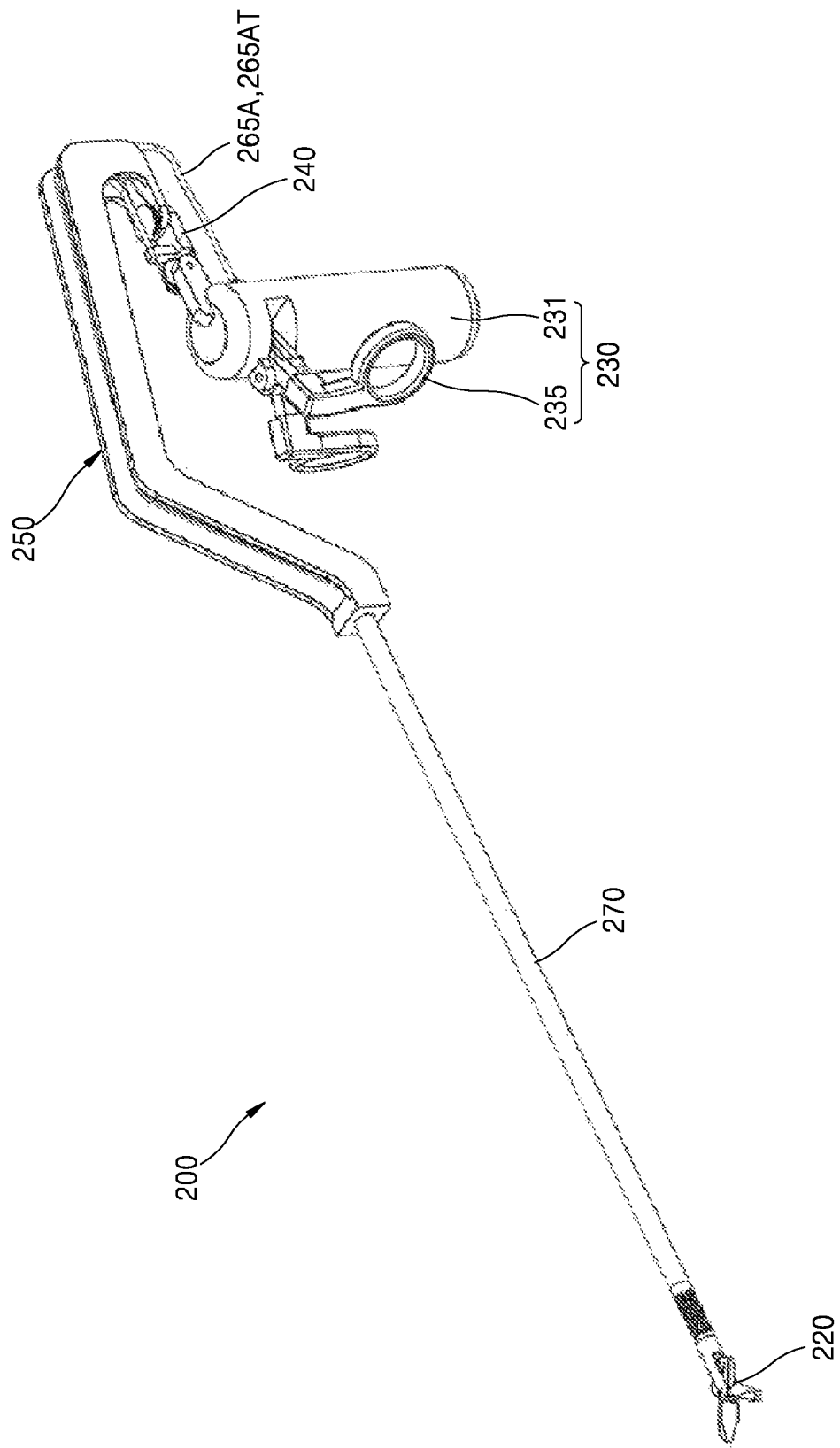
FIG. 20 is a perspective view of a surgical instrument according to another embodiment of the present disclosure.
Figure 21:
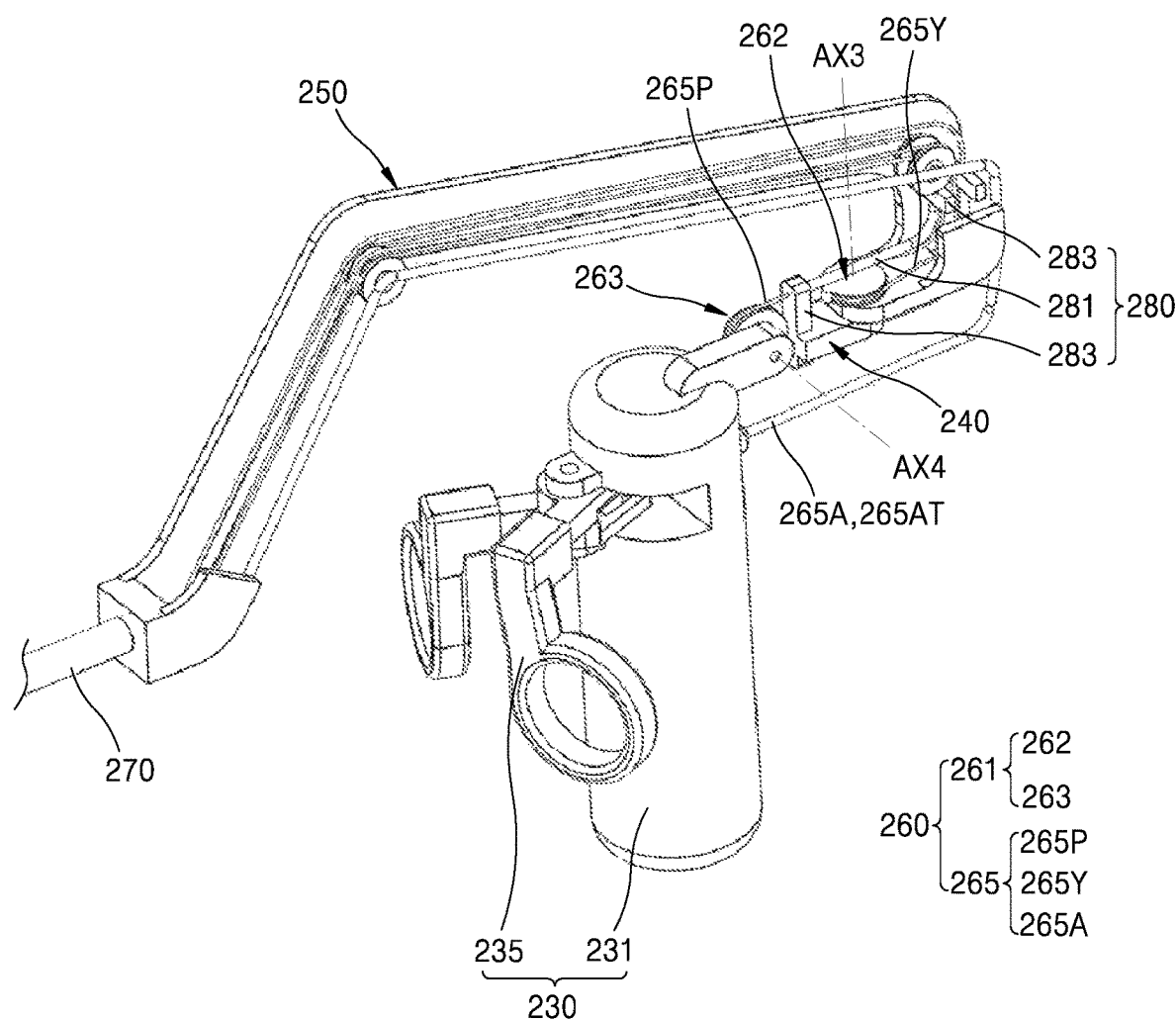
FIG. 21 is a partially cut-away view of a surgical instrument according to another embodiment of the present disclosure.
Figure 26:
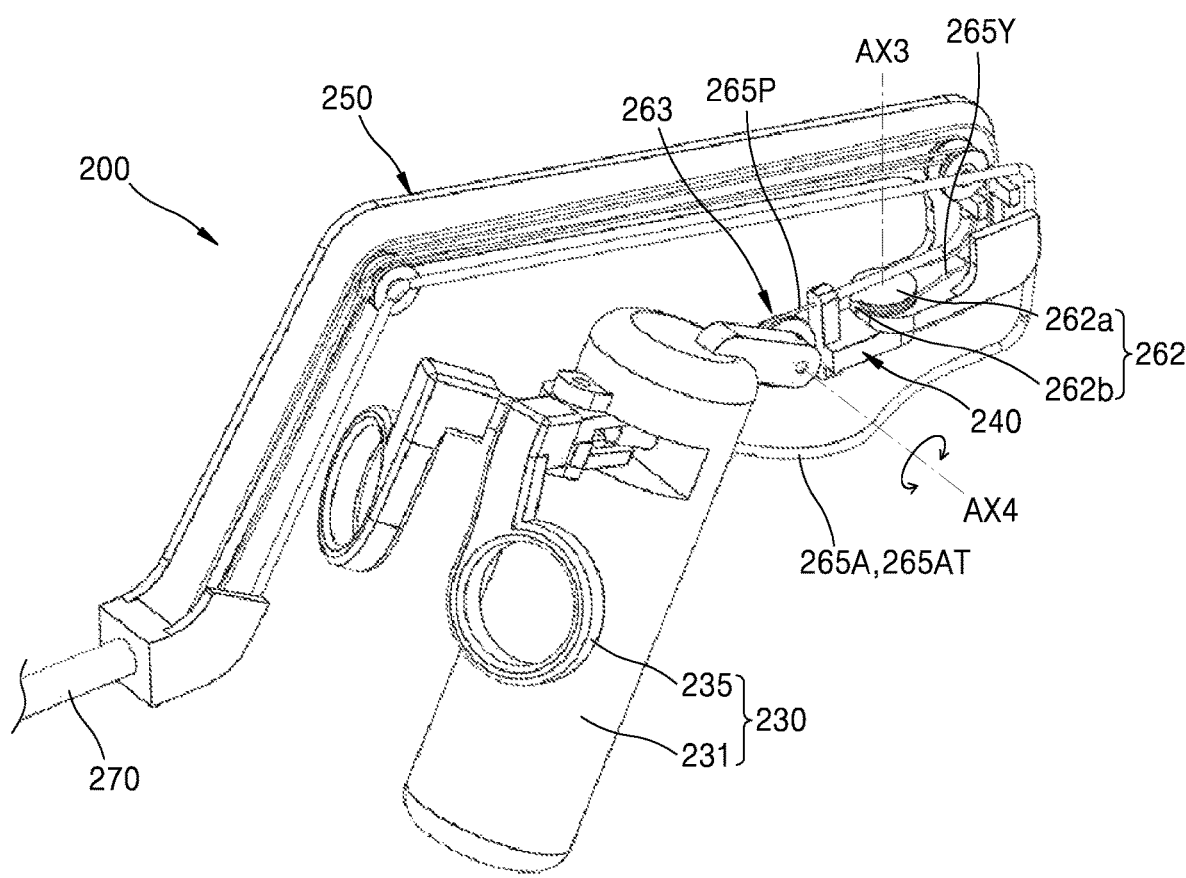
FIGS. 26 and 27 illustrate a pitch motion state of a surgical instrument according to another embodiment of the present disclosure.
Figure 27:
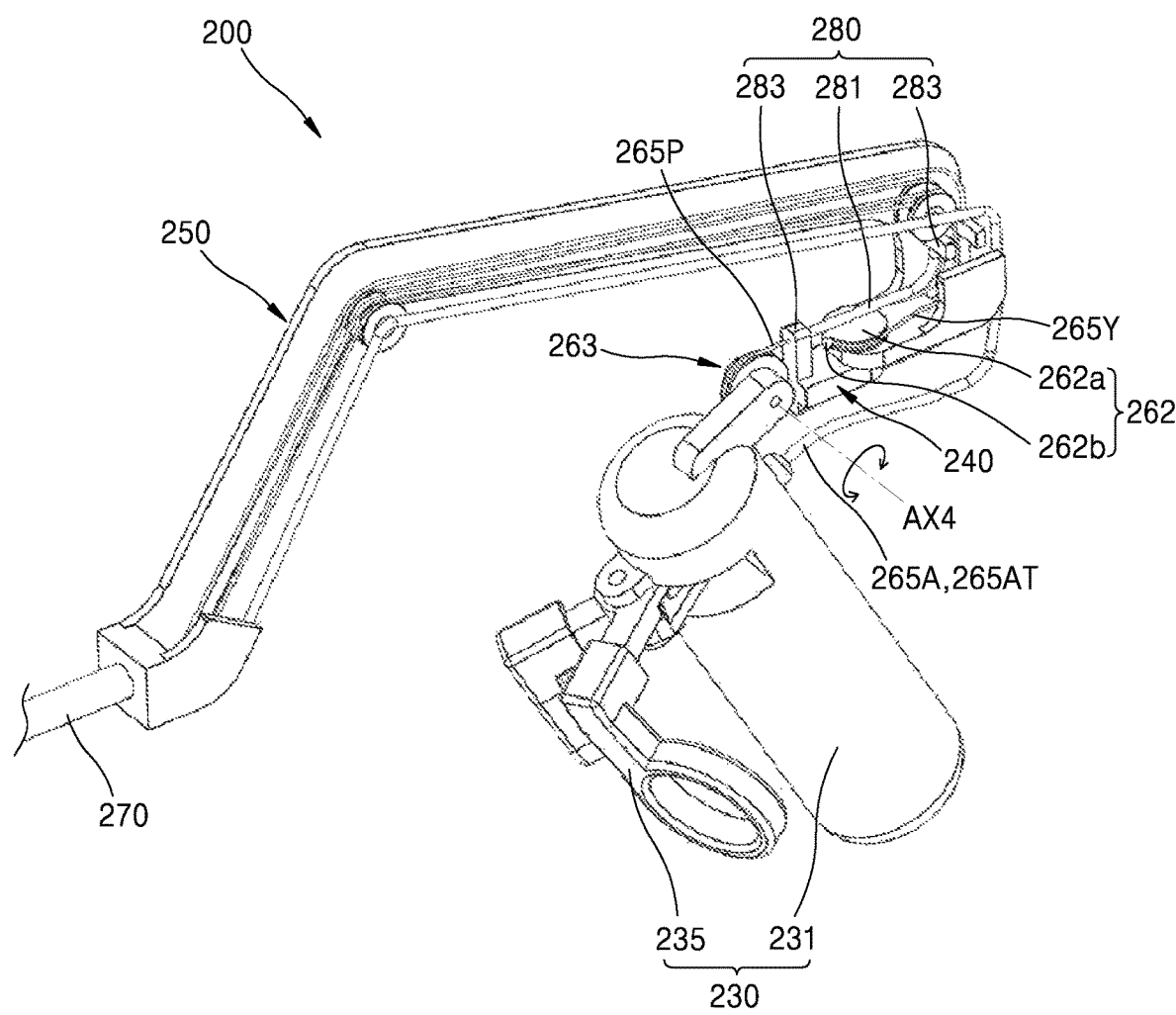
Figure 28:
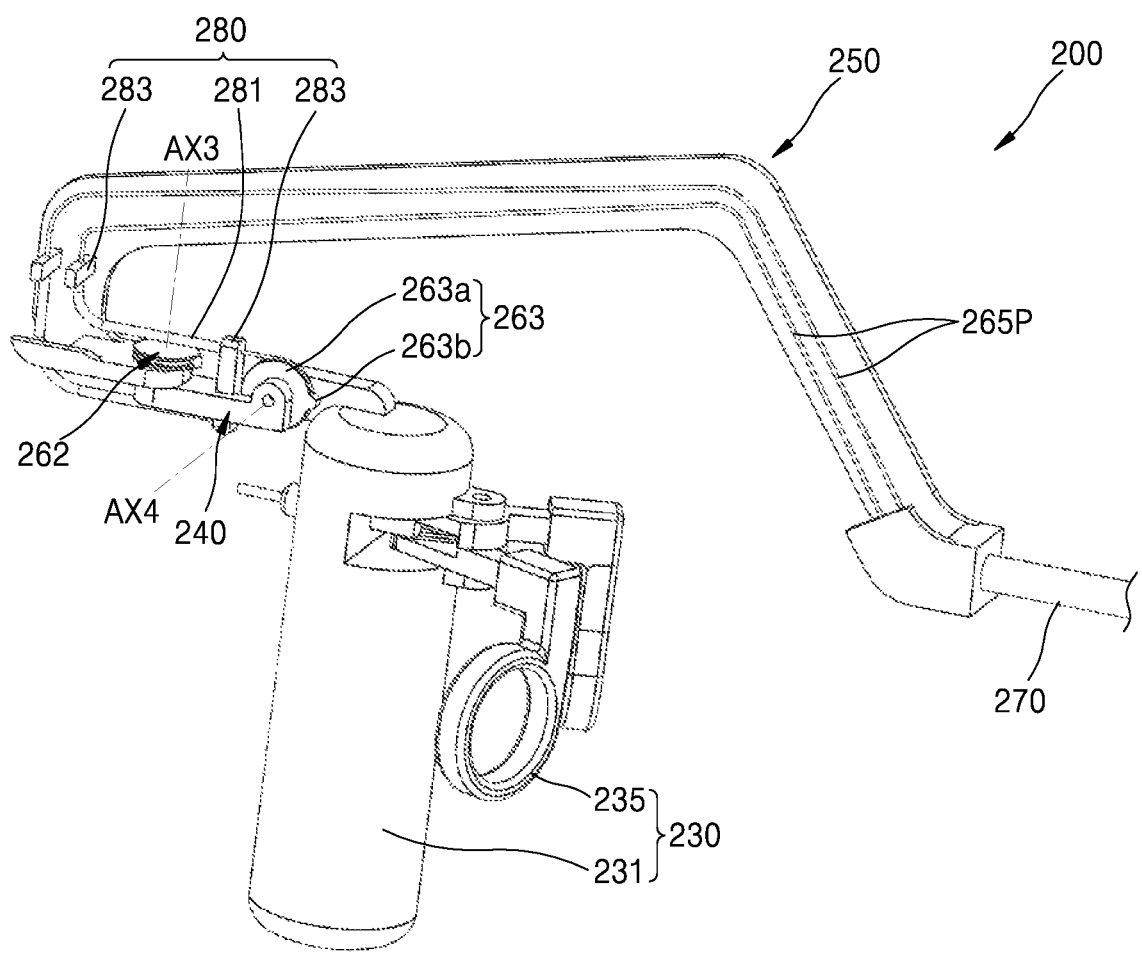
FIGS. 28 and 29 illustrate a bridge portion of a surgical instrument according to another embodiment of the present disclosure.
Figure 29:
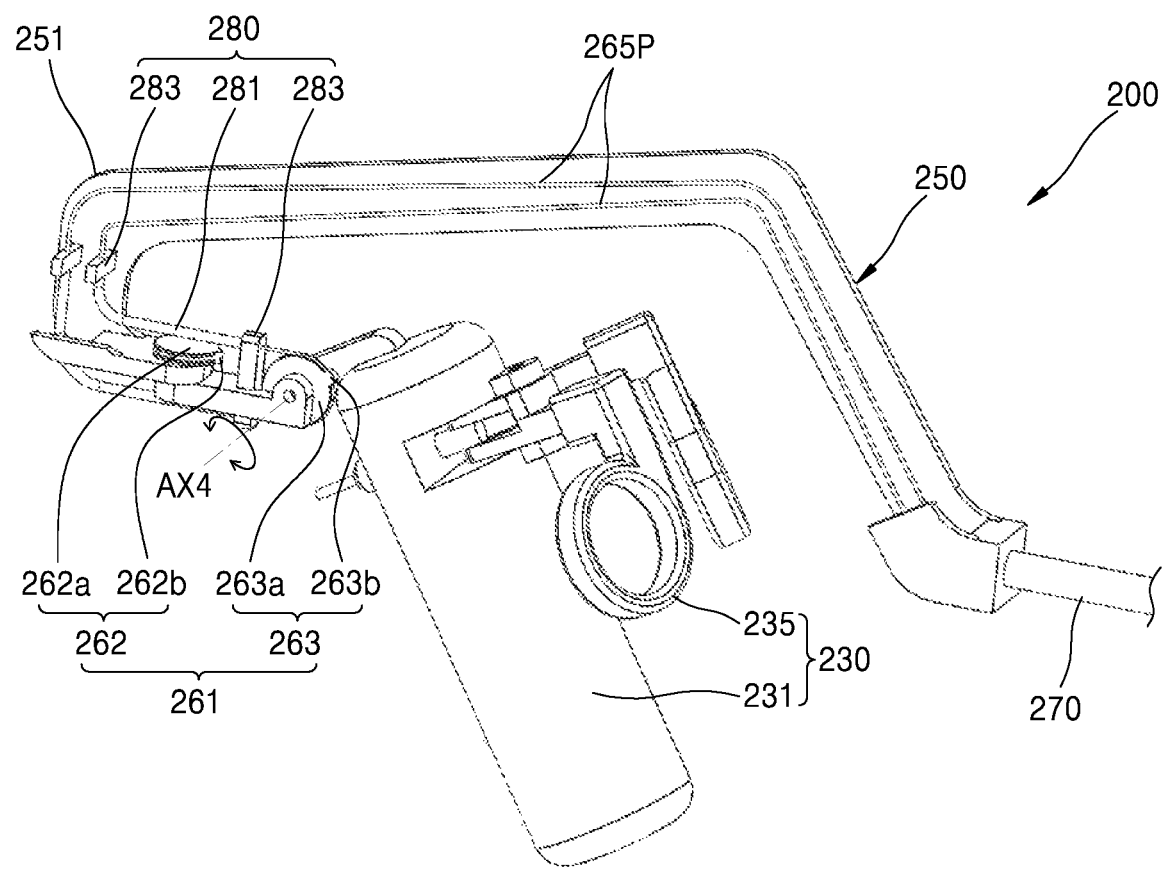

A surgical instrument according to another embodiment of the present disclosure is described below with reference to the accompanying drawings. FIG. 20 is a perspective view of a surgical instrument according to another embodiment of the present disclosure. FIG. 21 is a partially cutaway view of a surgical instrument according to another embodiment of the present disclosure. FIGS. 22 to 25 illustrate a yaw motion state of a surgical instrument according to another embodiment of the present disclosure. FIGS. 26 and 27 illustrate pitch motion state of a surgical instrument according to another embodiment of the present disclosure. FIGS. 28 and 29 illustrate a bridge portion of a surgical instrument according to another embodiment of the present disclosure.

In the specification about a surgical instrument 200 according to another embodiment of the present disclosure, a "first axis AX3" denotes a rotation center axis in performing a yaw motion, and a "second axis AX4" denotes a rotation center axis in performing a pitch motion.

Referring to FIGS. 1 to 6 and FIGS. 20 to 29, the surgical instrument 200 according to another embodiment of the present disclosure may include an end tool 220, a manipulation portion 230, a bridge portion 240, a frame portion 250, a driving force transmission portion 260, a connection portion 270, and a guide portion 280.

Referring to FIGS. 20, 21, 24, 26, and 28, the driving force transmission portion 260 according to another embodiment of the present disclosure transmits a motion of the manipulation portion 230 to the end tool 220 and may include a pulley portion 261 and a wire portion 265.

The pulley portion 261 according to another embodiment of the present disclosure is provided on the bridge portion 240 and the frame portion 250, and may include at least one pulley portion. The pulley portion 261 may include a yaw pulley 262 and a pitch pulley 263.

Figure 22:
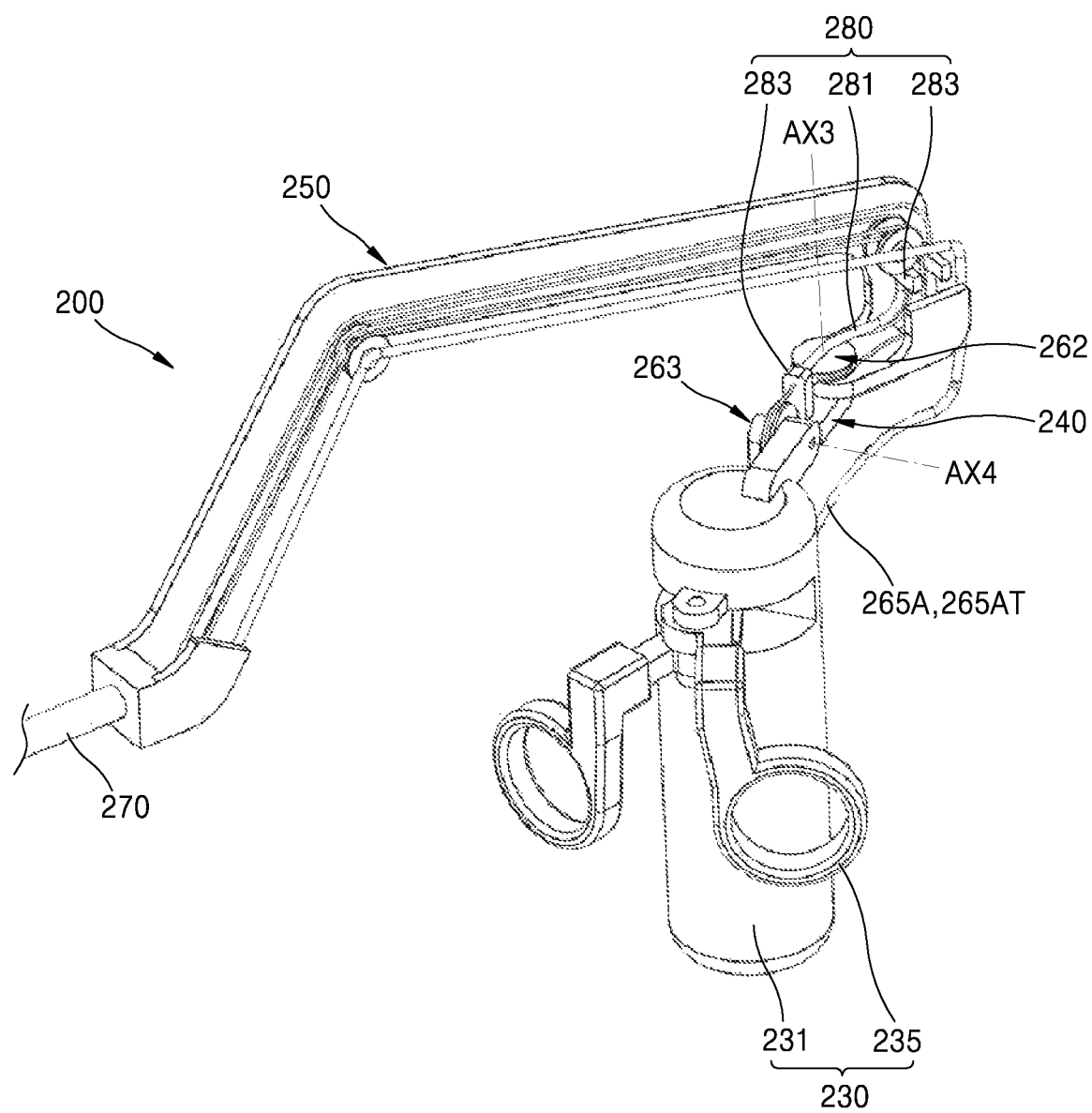
FIGS. 22 to 25 illustrate a yaw motion state of a surgical instrument according to another embodiment of the present disclosure.
Figure 23:
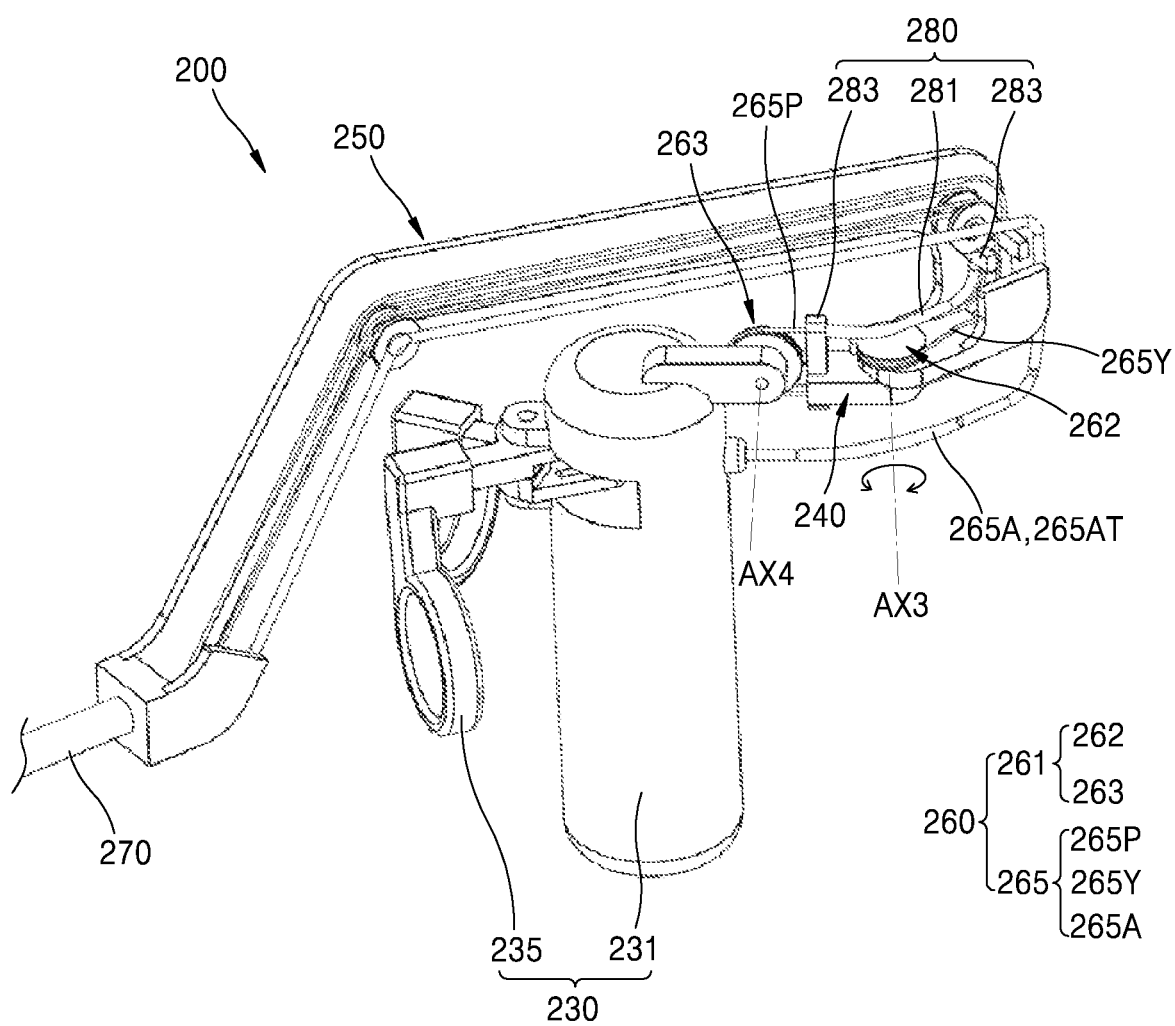

Referring to FIGS. 21 to 23, the yaw pulley 262 according to another embodiment of the present disclosure is rotatable around the first axis AX3 as a rotation center axis, and may include a pulley main body 262a and a wire coupling portion 262b.

The pulley main body 262a is connected to the bridge portion 240, and when a user grips and rotates the manipulation portion 230 around the first axis AX3 as a rotation center axis clockwise or counterclockwise, the bridge portion 240 connected to the manipulation portion 230 may be rotated around the first axis AX3 as a rotation center axis clockwise or counterclockwise with respect to the frame portion 250.

Accordingly, the pulley main body 262a rotates relative to the frame portion 250 on the frame portion 250 clockwise or counterclockwise, and may perform a yaw motion.

Figure 24:
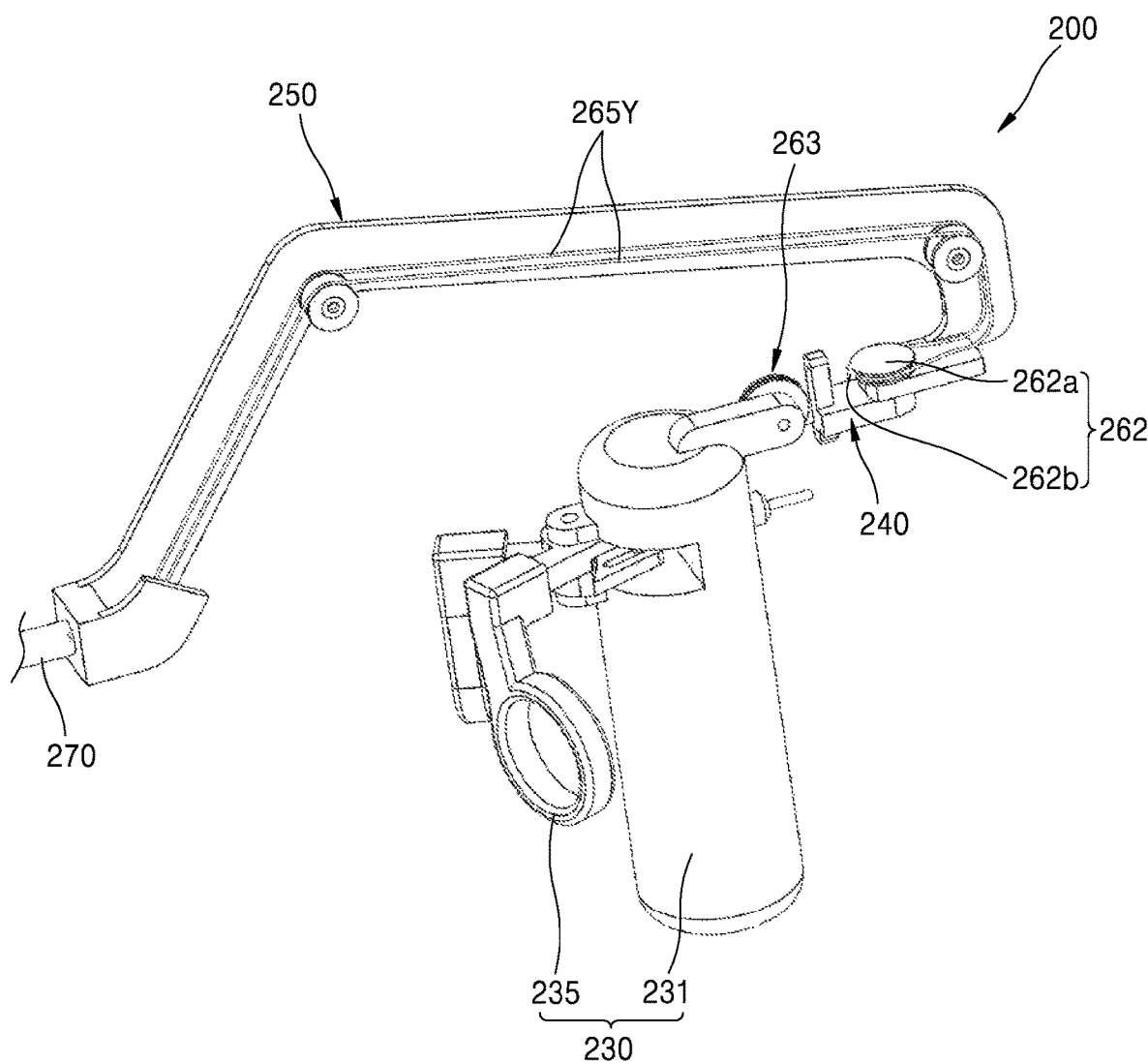
Figure 25:
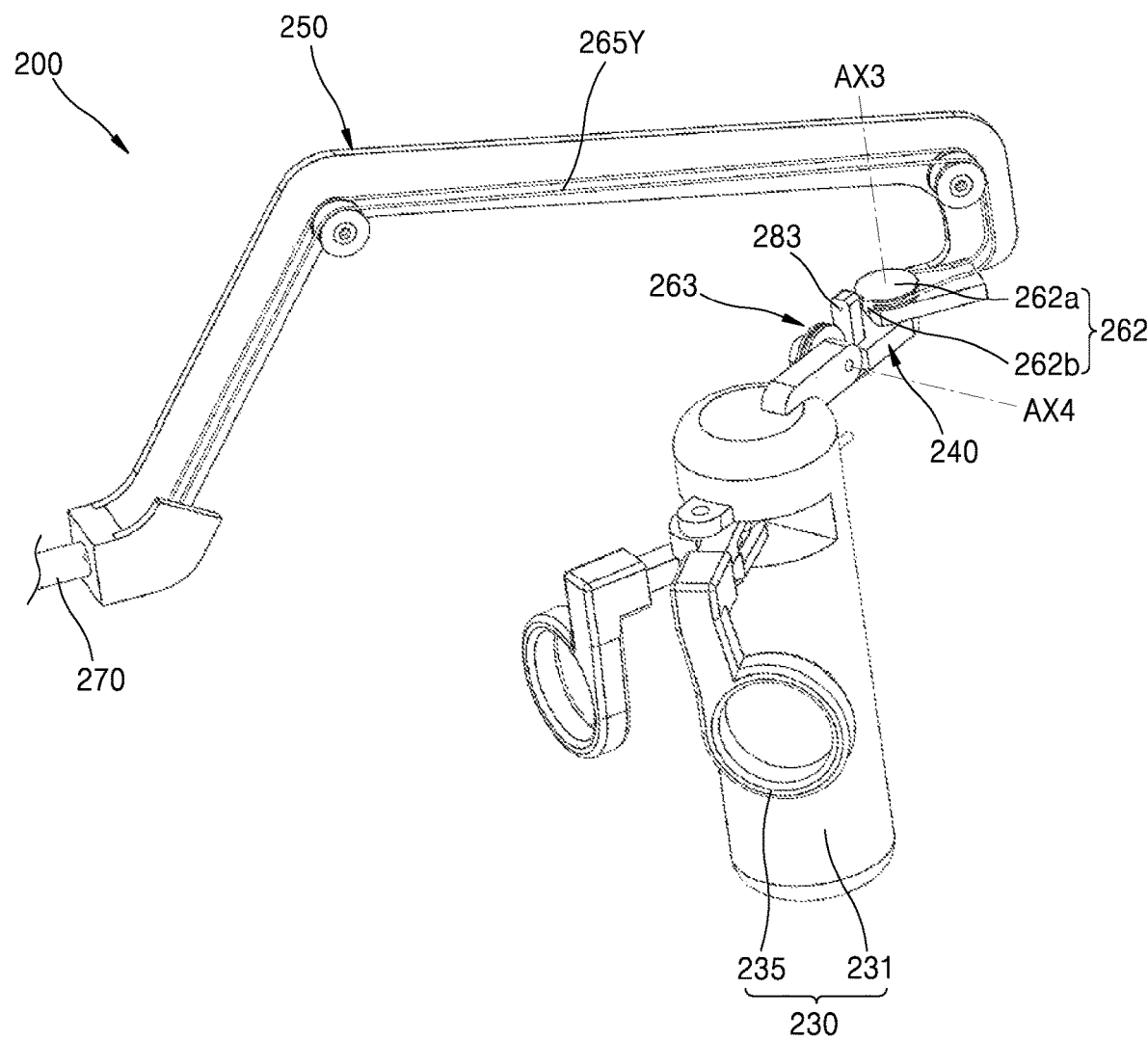

FIGS. 24 and 25 illustrate a state in which the frame portion 250 is partially cut away to visually express the inside of the frame portion 250 in the surgical instrument 200 according to another embodiment of the present disclosure, and a pitch wire 265P and an actuation wire 265A are removed to show the yaw pulley 262 and a yaw wire 265Y.

Referring to FIGS. 21 and 24, in the pulley main body 262a according to another embodiment of the present disclosure, the wire coupling portion 262b may be formed at a preset position so that the wire portion 265, particularly, the yaw wire 265Y, is coupled thereto.

In the present disclosure, although the wire coupling portion 262b protrudes along an outer circumferential surface of the pulley main body 262a, the present disclosure is not limited thereto, and various modifications are possible within a technical concept that the yaw wire 265Y is coupled to the pulley main body 262a so that the position of one end portion of the yaw wire 265Y is fixed.

Accordingly, when the user grips and rotates the manipulation portion 230 around the first axis AX3 as a rotation center axis clockwise or counterclockwise, the bridge portion 240 in association with the manipulation portion 230 is rotated around the first axis AX3 as a rotation center axis clockwise or counterclockwise with respect to the frame portion 250, thereby performing a yaw motion.

In other words, when the wire coupling portion 262b formed on the pulley main body 262a is rotated around the first axis AX3 as a rotation center axis clockwise or counterclockwise, the wire portion 265, particularly, the yaw wire 265Y, disposed on the pulley main body 262a at both sides with respect to the wire coupling portion 262b is wound or released so as to be moved inside the frame portion 250 and the connection portion 270, and thus the yaw motion of the manipulation portion 230 may be transmitted as the yaw motion of the end tool 220.

Referring to FIGS. 21 to 23, the pitch pulley 263 according to another embodiment of the present disclosure is rotatable around the second axis AX4 as a rotation center axis, and may include a pulley main body 263a and a wire coupling portion 263b.

The pulley main body 263a is connected to the bridge portion 240, and when the user grips and rotates the manipulation portion 230 around the second axis AX4 as a rotation center axis clockwise or counterclockwise, the bridge portion 240 connected to the manipulation portion 230 may be rotated clockwise or counterclockwise in associated therewith.

Accordingly, the pulley main body 263a is rotated around the second axis AX4 as a rotation center axis, on the bridge portion 240, clockwise or counterclockwise, thereby performing a pitch motion.

FIGS. 28 and 29 illustrate a state in which the frame portion 250 is partially cut away to visually express the inside of the frame portion 250 in the surgical instrument 200 according to another embodiment of the present disclosure, and the yaw wire 265Y and the actuation wire 265A are removed to show the pitch pulley 263 and the pitch wire 265P.

Referring to FIGS. 20, 21, 28, and 29, the wire coupling portion 263b may be formed on the pulley main body 263a at a preset position so that the wire portion 265, particularly, the pitch wire 265P is coupled thereto.

In the present disclosure, although the wire coupling portion 263b protrudes along an outer circumferential surface of the pulley main body 263a, the present disclosure is not limited thereto, and various modifications are possible within a technical concept that the pitch wire 265P is coupled to the pulley main body 263a so that the position of one end portion of the pitch wire 265P is fixed.

Accordingly, when the user grips the manipulation portion 230, particularly, a manipulation main body 231, and rotates the manipulation portion 230 and the bridge portion 240 connected to the manipulation portion 230 around the second axis AX4 as a rotation center axis with respect to the frame portion 250, the pitch pulley 263 in association with the manipulation portion 230 and the bridge portion 240 may be rotated around the second axis AX4 as a rotation center axis clockwise or counterclockwise.

In other words, when the wire coupling portion 263b formed on the pulley main body 263a is rotated around the second axis AX4 as a rotation center axis clockwise or counterclockwise, the wire portion 265, particularly, the pitch wire 265P, disposed on the pulley main body 263a at both sides with respect to the wire coupling portion 263b is wound or released so as to be moved inside the frame portion 250 and the connection portion 270, and thus the pitch motion of the manipulation portion 230 may be transmitted as the pitch motion of the end tool 220.

At least one pulley is provided in the frame portion 250 according to another embodiment of the present disclosure, and as the pitch wire 265P and the yaw wire 265Y are moved on the pulley, a movement path may be guided.

Referring to FIGS. 20 to 23 and FIGS. 26 to 29, the guide portion 280 according to another embodiment of the present disclosure may have one end portion connected to the bridge portion 240 and the other end portion provided on the frame portion 250, surround the wire portion 265 in a preset section, and guide a movement path of the wire portion 265.

Referring to FIGS. 20 to 23, the guide portion 280 according to another embodiment of the present disclosure may include a guide tube 281 and a pair of guide holders 283.

The guide tube 281 according to another embodiment of the present disclosure surrounds in a preset section the wire portion 265, particularly, the pitch wire 265P, and thus the pitch wire 265P may be moved inside the guide tube 281.

The pitch wire 265P is inserted into the guide tube 281, and thus the pitch wire 265P may be prevented from deviating from a preset path inside the guide tube 281.

In addition, a change in the length of the pitch wire 265P due to a shape change, for example, the pitch wire 265P has a bent portion inside the guide tube 281, may be prevented.

In addition, as the guide tube 281 connects the pair of guide holders 283 respectively provided on the bridge portion 240 and the frame portion 250, a distance between the pair of guide holders 283 may be maintained constant.

Accordingly, when the user grips the manipulation portion 230 and rotates the bridge portion 240 connected to the manipulation portion 230 around the first axis AX3 as a rotation center axis clockwise or counterclockwise with respect to the frame portion 250, thereby performing a yaw motion, the guide portion 280, particularly, the guide tube 281, and the pair of guide holders 283 coupled to each of both end portions of the guide tube 281 may prevent the user's yaw motion from affecting a change in the length of the pitch wire 265P that passes through the guide tube 281.

In other words, as the length of the pitch wire 265P is not changed, independency between the user's yaw motion and pitch motion may be maintained, and the yaw motion and pitch motion of the manipulation portion 230 may be intuitively transmitted as the yaw motion and pitch motion of the end tool 220.

Both end portions of the guide tube 281 according to another embodiment of the present disclosure may be coupled to the pair of guide holders 283. Accordingly, the length of the guide tube 281 connecting between the pair of guide holders 283 which are respectively fixedly coupled to the bridge portion 240 and the frame portion 250 may be fixed.

In addition, the wire portion 265, particularly, the pitch wire 265P, may be disposed as long as the length of the guide tube 281.

The guide tube 281 may be formed of a flexible material so as to be flexibly deformed corresponding to a case when the bridge portion 240 and the frame portion 250 perform a yaw motion by rotating relative to each other around the first axis AX3 as a rotation center axis.

Referring to FIGS. 28 and 29, the pair of guide holders 283 according to another embodiment of the present disclosure, which are penetrated by the wire portion 265, may be disposed on the bridge portion 240 and the frame portion 250 to be respectively coupled to both end portions of the guide tube 281.

The pair of guide holders 283 are respectively fixedly located at the bridge portion 240 and the frame portion 250, and the guide tube 281, which is formed as long as a preset length, may be connected between the pair of guide holders 283 that are respectively disposed on the bridge portion 240 and the frame portion 250.

Due to the guide tube 281 having a preset length and the pair of guide holders 283 coupled to both end portions of the guide tube 281, even when the bridge portion 240 and the frame portion 250 perform a pitch motion around the second axis AX4 as a rotation center axis, the positions of the pair of guide holders 283 are changed as the frame portion 250 is rotated, a distance between the pair of guide holders 283, that is, the length of the guide tube 281, may be maintained constant.

In addition, as the length of the guide tube 281 is maintained constant, even when the relative positions of the bridge portion 240 and the frame portion 250 are changed, the length of the wire portion 265, particularly, the pitch wire 265P, located inside the guide tube 281 may be maintained constant.

In other words, during the yaw motion of the bridge portion 240 connected to the manipulation portion 230 and the frame portion 250 rotating relative to each other around the first axis AX3 as a rotation center axis, the length of the pitch wire 265P may be maintained constant in a preset section, particularly, the length of the guide portion 280.

In addition, as the distance between the pair of guide holders 283 respectively disposed on the bridge portion 240 and the frame portion 250, and the length of the guide tube 281 disposed between the pair of guide holders 283, are maintained constant, during the yaw motion of the manipulation portion 230, the length of the pitch wire 265P in the guide portion 280 may be maintained constant, and thus the yaw motion and the pitch motion may be independently performed without affecting each other.

In the surgical instrument 200 according to another embodiment of the present disclosure, except that the bridge portion 240 performs a yaw motion of rotating around the first axis AX3 as a rotation center axis clockwise or counterclockwise with respect to the frame portion 250, the manipulation portion 230 connected to the bridge portion 240 performs a pitch motion of rotating around the second axis AX4 as a rotation center axis clockwise or counterclockwise with respect to the bridge portion 240, the configuration, operating principle, and effect of the end tool 220, the manipulation portion 230, the bridge portion 240, the frame portion 250, the driving force transmission portion 260, the connection portion 270, and the guide portion 280 are the same as those of the surgical instrument 100 according to an embodiment of the present disclosure, and thus detailed descriptions thereof are omitted within the scope of redundancy.

The particular implementations shown and described herein are illustrative examples of the disclosure and are not intended to otherwise limit the scope of the disclosure in any way. For the sake of brevity, conventional electronics, control systems, software development and other functional aspects of the systems may not be described in detail. Furthermore, the connecting lines, or connectors shown in the various figures presented are intended to represent functional relationships and/or physical or logical couplings between the various elements. It should be noted that many alternative or additional functional relationships, physical connections or logical connections may be present in a practical device. Moreover, no item or component is essential to the practice of the disclosure unless the element is specifically described as "essential" or "critical."

The use of the terms "a" and "an" and "the" and similar referents in the context of describing the disclosure (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The disclosure is not limited to the described order of the steps. The use of any and all examples, or language (e.g., "such as") provided herein, is intended merely to better illuminate the disclosure and does not pose a limitation on the scope of the disclosure unless otherwise claimed. Numerous modifications and adaptations will be readily apparent to one of ordinary skill in the art without departing from the spirit and scope of the disclosure.

The embodiments of the disclosure can be written as computer programs and can be implemented in general-use digital computers that execute the programs using a computer readable recording medium. In this state, the medium may continuously store a program that can be executed by a computer, or may store a program for execution or download.

Furthermore, the medium may be various recording devices or storing devices in which single or several hardware are combined, which it not limited to a medium that is directly accessed to a computer system and may be present over a network in a distribution manner. Examples of the medium include magnetic storage media such as floppy disks or hard disks, optical recording media such as CD-ROMs or DVDs, magneto-optical medium such as floptical disks, and Rom, RAM, flash memory, etc., which are configured to store program instructions. Furthermore, examples of other media may include application stores for distributing applications, sites for supplying or distributing other various software, and recording media or storing media managed at servers.

In the above, although the present disclosure has been described by specific matters such as specific constituent elements or the like, limited embodiments, and the drawings, these are provided to help the overall understanding of the present disclosure, and the present disclosure is not limited to the above embodiments, and those skilled in the art to which the present disclosure pertains could make various modifications and changes from these descriptions.

Accordingly, the spirit e present disclosure is not limited to the above-described embodiments, and it may be said that not only the claims to be described later, but also all scope that is equivalent to or equivalently changed from the claims would belong to the scope of the spirit of the present disclosure.

INDUSTRIAL APPLICABILITY

The present disclosure provides a surgical instrument. Furthermore, the embodiments of the present disclosure may be applied to manually operated instruments for use in industrially used laparoscopic surgery or various surgical procedures.

The invention claimed is:

1. A surgical instrument comprising:
   an end tool capable of rotating in at least two directions;
   a connection portion having a hollow inside and one end portion to which the end tool is connected;
   a frame portion having a hollow inside and coupled to another end portion of the connection portion opposite to the one end portion of the connection portion connected to the end tool;
   a bridge portion connected to the frame portion and capable of pitch motion with respect to the frame portion around a first axis as a pitch axis;
   a manipulation portion connected to the bridge portion and capable of yaw motion with respect to the bridge portion around a second axis as a yaw axis, the manipulation portion being capable of controlling a pitch motion, a yaw motion, and an actuation motion of the end tool;
   a driving force transmission portion that comprises a pulley portion including a pitch pulley and a yaw pulley which are rotatably provided on the bridge portion or the frame portion, and a wire portion including a pitch wire and a yaw wire which have one end portion connected to the end tool, and transmits a motion of the manipulation portion to the end tool; and
   a guide portion that has one end portion provided on the bridge portion and another end portion provided on the frame portion, surrounds the wire portion in a preset section, and guides a movement path of the wire portion,
   wherein the yaw wire is inserted through the guide portion, and
   after passing through the frame portion, the yaw wire is directly connected to the yaw pulley without passing through another pulley.

2. The surgical instrument of claim 1, wherein the manipulation portion, the frame portion, and the bridge portion are rigid-linked with each other.

3. The surgical instrument of claim 1, wherein the guide portion comprises:
   a guide tube surrounding the wire portion in a preset section; and
   a pair of guide holders penetrated by the wire portion and disposed on the bridge portion and the frame portion to be coupled to each of both end portions of the guide tube.

4. The surgical instrument of claim 3, wherein the guide tube comprises a flexible material.

5. The surgical instrument of claim 3, wherein
   the surgical instrument is configured that even if a position of each of the pair of guide holders is changed, an entire length of the guide tube is maintained constant and a length of the yaw wire in the guide tube in the preset section where the guide tube is provided is also maintained constant, so that when the pitch motion is performed, the yaw wire in the guide tube is not affected by the pitch motion.

6. The surgical instrument of claim 1, wherein
   the pitch pulley is rotatable around the first axis as a rotation center axis; and
   the yaw pulley is rotatable around the second axis as a rotation center axis.

7. The surgical instrument of claim 6, wherein the yaw pulley is disposed closer to the end tool than the pitch pulley is.

8. The surgical instrument of claim 6, wherein
   the yaw pulley is disposed spaced apart from the frame portion and provided on the manipulation portion to be rotated on the bridge portion, and
   the pitch pulley is provided on the bridge portion to be rotated on the frame portion.

9. A surgical instrument comprising:
   an end tool capable of rotating in at least two directions;
   a connection portion having a hollow inside and one end portion to which the end tool is connected;

a frame portion having a hollow inside and coupled to another end portion of the connection portion opposite to the one end portion of the connection portion connected to the end tool;

a bridge portion connected to the frame portion and capable of yaw motion with respect to the frame portion around a first axis as a yaw axis;

a manipulation portion connected to the bridge portion and capable of pitch motion with respect to the bridge portion around a second axis as a pitch axis, the manipulation portion being capable of controlling a pitch motion, a yaw motion, and an actuation motion of the end tool;

a driving force transmission portion that comprises a pulley portion including a pitch pulley and a yaw pulley which are rotatably provided on the bridge portion or the frame portion, and a wire portion including a pitch wire and a yaw wire which have one end portion connected to the end tool, and transmits a motion of the manipulation portion to the end tool; and a guide portion that has one end portion provided on the bridge portion and another end portion provided on the frame portion, surrounds the wire portion in a preset section, and guides a movement path of the wire portion, wherein the pitch wire is inserted through the guide portion, and after passing through the frame portion, the pitch wire is directly connected to the pitch pulley without passing through another pulley.

10. The surgical instrument of claim 9, wherein the manipulation portion, the frame portion, and the bridge portion are rigid-linked with each other.

11. The surgical instrument of claim 9, wherein the guide portion comprises:

a guide tube surrounding the wire portion in a preset section; and a pair of guide holders penetrated by the wire portion and disposed on the bridge portion and the frame portion to be coupled to each of both end portions of the guide tube.

12. The surgical instrument of claim 11, wherein the guide tube comprises flexible material.

13. The surgical instrument of claim 11, wherein the surgical instrument is configured that even if a position of each of the pair of guide holders is changed, an entire length of the guide tube is maintained constant and a length of the pitch wire in the guide tube in the preset section where the guide tube is provided is also maintained constant, so that when the yaw motion is performed, the pitch wire in the guide tube is not affected by the yaw motion.

14. The surgical instrument of claim 9, wherein the yaw pulley is rotatable around the first axis as a rotation center axis; and the pitch pulley is rotatable around the second axis as a rotation center axis.

15. The surgical instrument of claim 14, wherein the pitch pulley is disposed closer to the end tool than the yaw pulley is.

16. The surgical instrument of claim 14, wherein the pitch pulley is disposed spaced apart from the frame portion and provided on the manipulation portion to be rotated on the bridge portion, and the yaw pulley is provided on the bridge portion to be rotated on the frame portion.

* * * * *